United States Patent
Ramalho Ferreira et al.

(10) Patent No.: US 12,222,364 B2
(45) Date of Patent: Feb. 11, 2025

(54) DETECTION OF INCORRECT ARRANGEMENT OF INERTIAL MEASUREMENTS UNITS OF A MOTION TRACKING SYSTEM

(71) Applicant: SWORD HEALTH S.A., Oporto (PT)

(72) Inventors: Marta Maria Ramalho Ferreira, Oporto (PT); Ivo Jorge Ramos De Magalhães, Oporto (PT); Luís Ungaro Pinto Coelho, Oporto (PT); Pedro Henrique Oliveira Santos, Oporto (PT); Ivo Emanuel Marques Gabriel, Oporto (PT); Ana Clara Ferreira Matos, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 283 days.

(21) Appl. No.: 17/641,702

(22) PCT Filed: Sep. 4, 2020

(86) PCT No.: PCT/EP2020/074811
§ 371 (c)(1),
(2) Date: Mar. 9, 2022

(87) PCT Pub. No.: WO2021/048022
PCT Pub. Date: Mar. 18, 2021

(65) Prior Publication Data
US 2022/0299542 A1    Sep. 22, 2022

(30) Foreign Application Priority Data
Sep. 10, 2019    (EP) .................................... 19398009

(51) Int. Cl.
*G01P 15/08*    (2006.01)
*G01P 15/14*    (2013.01)
(Continued)

(52) U.S. Cl.
CPC .............. *G01P 15/08* (2013.01); *G01P 15/14* (2013.01); *G01P 21/00* (2013.01); *G16H 20/30* (2018.01); *G16H 40/63* (2018.01)

(58) Field of Classification Search
CPC .......... G01P 15/08; G01P 15/14; G01P 15/00; G01P 15/0891; G01P 15/003;
(Continued)

(56) References Cited

U.S. PATENT DOCUMENTS 9,081,436 B1 * 7/2015 Berme .................... G06F 3/013
11,592,512 B2 * 2/2023 Vissiere ................. G01V 13/00
(Continued)

FOREIGN PATENT DOCUMENTS

EP    3734229 A1 * 11/2020 ............... A61B 5/11
EP    3792928 A1    3/2021
(Continued)

OTHER PUBLICATIONS

"Inertial measurement unit", Wikipedia, Mar. 2, 2016, p. 1-11, URL:https://en.wikipedia.org/w/index.php?title=Inertial_measurement_unit&oldid=707846453.
(Continued)

*Primary Examiner* — Jeffrey P Aiello
(74) *Attorney, Agent, or Firm* — SCHWEGMAN LUNDBERG & WOESSNER, P.A.

(57) ABSTRACT

A method for physical exercise using a motion tracking system having a computing device and inertial measurement units adapted to be arranged on body members of a person. The method includes: digitally processing first sets of measurements provided by the units to determine whether and adjust the operation of the motion tracking system when: any of the units is arranged on a body member with an orientation outside of a predetermined orientation range for a unit on that body member; and/or two or more units
(Continued)

arranged on interchanged body members according to the predetermined unit arrangement; adjusting the operation of the motion tracking system when the computing device determines, based on at least the first sets of measurements, that: at least one unit has an orientation outside of the predetermined orientation range, and/or two or more units are arranged on interchanged body members; and digitally processing second sets of measurements.

20 Claims, 4 Drawing Sheets

(51) Int. Cl.
*G01P 21/00* (2006.01)
*G16H 20/30* (2018.01)
*G16H 40/63* (2018.01)

(58) Field of Classification Search
CPC .. G01P 15/18; G01P 21/00; G01P 3/50; G01P 3/00; G01P 3/44; G01P 13/00; G16H 20/30; G16H 40/63; G16H 40/67; G16H 50/20; G16H 50/50; A61B 2562/0219; A61B 5/118; A61B 5/0002; A61B 5/6807; A61B 5/6804; A61B 5/02438; A61B 5/112; A61B 5/1123; A61B 5/6802; A61B 2503/10; G01C 22/006; G01C 5/00; G01C 17/38; G01C 21/10; G01C 21/188; G01C 21/1654; G01C 21/16; G01C 19/00; G01C 1/00; G06F 3/0346; G06F 3/011; G06F 3/014; G06F 15/00; G06F 17/18; A63B 24/0062; A63B 2220/40; A63B 2220/62; A63B 2220/16; A63B 2220/44; A63B 2220/836; A63B 71/0605; A63B 71/10; A63B 2024/0071; A63B 69/0028
USPC ............. 73/1.37, 510, 1.38, 1.75, 1.79, 488, 73/865.4, 1.77; 700/83, 108; 702/141, 702/150, 19, 188, 182, 160, 94, 189, 104, 702/85, 183, 152, 127, 151, 153, 95, 1
See application file for complete search history.

(56) References Cited

U.S. PATENT DOCUMENTS

| | | | |
|---|---|---|---|
| 2014/0303524 A1* | 10/2014 | Chen | A61B 5/7225 600/595 |
| 2018/0188284 A1* | 7/2018 | Douglas | G06V 40/23 |
| 2018/0330810 A1* | 11/2018 | Gamarnik | G16H 10/20 |
| 2020/0193677 A1* | 6/2020 | Vaganov | A63F 13/65 |
| 2021/0306811 A1* | 9/2021 | Hapola | G01C 21/165 |

FOREIGN PATENT DOCUMENTS

| | | |
|---|---|---|
| EP | 4029027 A1 | 7/2022 |
| WO | 2019243438 A1 | 12/2019 |
| WO | WO-2021048022 A1 | 3/2021 |

OTHER PUBLICATIONS

International Search Report issued Nov. 25, 2020 re: Application No. PCT/EP2020/074811, pp. 1-4, citing: US 2014/0303524 A1, US 2018/0330810 A1, Wikipedia "Inertial measurement . . . " and US 2018/0188284 A1.
Written Opinion issued Nov. 25, 2020 re: Application No. PCT/EP2020/074811, pp. 1-15, citing: US 2014/0303524 A1, US 2018/0330810 A1, Wikipedia "Inertial measurement . . . " and US 2018/0188284 A1.
European Application Serial No. 20764681.1, Response to Communication pursuant to Rules 161(2) and 162 EPC filed Nov. 10, 2022, 24 pgs.
European Application Serial No. 19398009.1, Extended European Search Report mailed Mar. 23, 2020, 10 pgs.
International Application Serial No. PCT/EP2020/074811, International Preliminary Report on Patentability mailed Mar. 24, 2022, 17 pgs.
PCT Direct letter submitted with International Application Serial No. PCT/EP2020/074811 mailed Sep. 1, 2020, 50 pgs.
European Application Serial No. 20764681.1, Communication Pursuant to Article 94(3) EPC mailed Nov. 13, 2024, 7 pgs.

* cited by examiner

DETECTION OF INCORRECT ARRANGEMENT OF INERTIAL MEASUREMENTS UNITS OF A MOTION TRACKING SYSTEM

TECHNICAL FIELD

The present disclosure relates to the field of systems for tracking motion of a person. More particularly, the disclosure relates to the detection of incorrect arrangement of inertial measurement units of the motion tracking system on body members of the person.

BACKGROUND

Motion tracking or motion capture is becoming a key technique in different applications in which the movement of a target such as a person is an important part in one or more processes of the applications.

An application growing in popularity is the physical rehabilitation of people while being monitored with a motion tracking system. The motion tracking system enables the physical rehabilitation of a person without the presence of a therapist. The person may improve the physical condition thereof by performing a number of physical exercises even if not directly supervised by the therapist but by the motion tracking system, hence the person may even perform the exercises at home.

A computing device processes measurements of the motion tracking system in order to assess how the person performs the physical exercises. The motion tracking system may include inertial measurements units, i.e. IMUs, for motion tracking of a target; the IMUs are adapted to be arranged on the target and may include one or more sensing devices such as gyroscopes, accelerometers, magnetometers, etc. The computing device is connected to the IMUs and processes the measurements of one or several of these sensing devices, and by processing said measurements the computing device determines the movement sequence of the target, at least the movement sequence of the tracked parts of the target (i.e. those with an IMU arranged thereon).

One of the main problems that such motion tracking systems have is that they require the person to arrange the IMUs on the different body members. The person may inadvertently incorrectly place one or more units on respective body members (e.g. tilted with respect to the segment of the body member), inadvertently swap one unit by another thereby swapping the measurements thereof, or inadvertently arrange one or more units on body members different than those to be tracked. This problem influences the overall user experience and may, ultimately, result in the injury of the user because the assessment of the physical exercises performed by the person is incorrect.

Patent document US2014/303524A1 provides calibration of a motion tracking system by mapping body segments of a skeleton and sensors attached to a person. In order to perform the calibration, the user needs to place the feet or hands thereof on predetermined positions of a template for receiving orientation signals whereby the calibration can be effected. Likewise, the calibration requires the solving of kinematic chain equations.

It would be convenient to have a way to determine whether any inertial measurement unit of a motion tracking system for the physical exercise of a person has been incorrectly arranged with respect to a predetermined unit arrangement based on the physical exercise(s) or movement(s) to be performed by the person. It would also be preferable if, once it is determined that at least one unit may have been incorrectly arranged, the motion tracking system were capable of automatically adjusting the motion tracking procedure so that the physical exercise may be properly assessed without the intervention of the person (which could entail, for instance, the rearrangement of the incorrectly arranged unit or units).

SUMMARY

A first aspect of the disclosure relates to a method for physical exercise of a person using a motion tracking system, the motion tracking system comprising a computing device and a plurality of inertial measurement units adapted to be arranged on body members of the person, the method comprising:

arranging each unit of the plurality of units on a different body member of the person according to a predetermined unit arrangement;

providing a first set of measurements, by each unit of the plurality of units, of the person with the units arranged thereon standing still and/or performing a first predetermined movement, the first predetermined movement involving movement of at least one or more body members having a unit arranged thereon;

digitally processing, the computing device, at least the first sets of measurements so as to determine whether:
  any unit of the plurality of units is arranged on a body member of the person with an orientation outside of a predetermined orientation range for a unit on that body member; and/or
  two or more units of the plurality of units may be arranged on interchanged body members of the person according to the predetermined unit arrangement;

adjusting the operation of the motion tracking system when the computing device determines, based on at least the first sets of measurements, that: at least one unit has an orientation outside of the predetermined orientation range, and/or two or more units are arranged on interchanged body members;

providing a second set of measurements, by each unit of the plurality of units, of the person with the units arranged thereon performing a second predetermined movement, the second predetermined movement involving movement of at least one or more body members having a unit arranged thereon; and digitally processing, the computing device, the second sets of measurements after the step of adjusting the operation of the motion tracking system so as to determine whether the person has performed the second predetermined movement according to a set of predetermined movement constraints.

The person is able to exercise with the supervision of the computing device and problems arising from an incorrect arrangement of the units, i.e. IMUs, can be fixed digitally in an automatic manner, and/or can be presented to the person for corrective action by herself/himself; in the former, the rearrangement of the IMUs is not necessary, whereas in the latter the person is to rearrange the IMUs that are incorrectly arranged. In both cases, the computing device digitally determines based on at least the first sets of measurements, which include one or more of orientations of a gyroscope, whether any unit may have been arranged incorrectly with respect to the position of the unit(s) on the body member(s) and/or the orientation of the unit(s) on the body member(s), and/or the placement of units on interchanged body members. Each first set of measurements includes e.g. orientations and/or accelerations of respective units, which can be provided by e.g. a gyroscope, an accelerometer, a magnetometer, or a combination thereof.

The predetermined unit arrangement enables the computing device to process the measurements of the IMUs for determining the movement sequence of the person or at least the tracked parts thereof. Further, the computing device is provided with predetermined position and orientation constraints; said constraints set the expected position and orientation of the IMUs on the body members for accurate motion sequence determination. In this sense, the predetermined unit arrangement establishes which body members shall have a unit arranged thereon, and the predetermined unit arrangement that the computing device is provided with includes a correspondence between IMUs and body members; the predetermined position and orientation constraints establish how the units should be positioned and oriented on the body members for a given predetermined unit arrangement so that the computing device determines how each body member is oriented and/or moves based on the measurements provided by the respective unit, for example when the person is standing still and/or performing one or more movements, such as the first predetermined movement. That is to say, the computing device makes the determination based on the orientation measurements and/or the acceleration measurements provided by the units and the behavior thereof in accordance with the predetermined unit arrangement and the constraints when the person stands still and/or performs the first predetermined movement; the computing device assumes that the person behaves in this way for an accurate determination of incorrect placement or orientation of units. Upon processing the measurements of each unit, the computing device at least determines how the tracked parts are positioned and move, thereby tracking the motion of the person.

A number of predetermined unit arrangements is possible since each one of them is suitable for tracking one or more movements to be performed by the person. By way of example, one predetermined unit arrangement establishes that a first IMU is to be arranged on an upper arm of the right arm of the person, a second IMU is to be arranged on a lower arm of the right arm, and a third IMU is to be arranged on the chest of the person. The predetermined position and orientation constraints establish that, for instance but without limitation, the first IMU is to be arranged at the middle part of the segment of the upper arm, and that it is both front-facing and (if the IMU comprises an accelerometer) with the accelerometer's gravity vector (that points in a vertical direction and downwards) aligned or substantially aligned with the corresponding unit axis when the arm is in a rest position and laying parallel to the chest, the second IMU is to be arranged similarly on the lower arm, and the third IMU is to be arranged at the top part of the chest. When a physical exercise involving, for example, movement of the legs is to be performed by the person as part of her/his physical exercise, the predetermined unit arrangement establishes that IMUs are to be arranged on one or both legs, and in one or more parts thereof, and possibly one or more IMUs may have to be arranged on other body members as well. The predetermined unit arrangement or arrangements may be stored in at least one memory of the computing device together with the predetermined position and orientation constraints (which, in some embodiments, are already incorporated into the predetermined unit arrangement stored in the memory), and may be presented with presenting means (e.g. a screen, audio output means such as loudspeakers, a vibrating device, etc.) to the person so that proper arrangement or rearrangement (when the physical exercise to be performed changes) of the IMUs can be effected, in terms of body members, position and orientation. In some embodiments, the presenting means are part of the motion tracking system whereas, in some other embodiments, the presenting means are not part of the motion tracking system, yet the computing device is connected with the presenting means so as to transmit data thereto.

Based on the predetermined orientation constraints, the computing device determines if there is any IMU with an orientation not within a predetermined orientation range corresponding to an expected range of orientations for a unit arranged on a given body member while the person performs the first predetermined movement and/or stands still, for example whether an IMU has an orientation indicative of an upside down arrangement on the body member (e.g. when the orientation measurements differ by more than 90° with respect to the expected values), or an IMU has an orientation indicative of a tilted arrangement on the body member (i.e. the IMU is not aligned with the segment of the body member). Further, the computing device additionally or alternatively determines if two or more IMUs may have been swapped and, thus, arranged on body members that were supposed to have a different IMU according to the predetermined unit arrangement. To this end, the computing device digitally processes the first predetermined movement and/or the standing still so as to have data indicative of the measurements it expects from each unit; in some cases, this processing is made beforehand and digitally stored so that the processor or processors of the computing device can retrieve the data whenever necessary. A predetermined set of thresholds is incorporated into said data so as to accept some deviations from a perfectly executed first predetermined movement.

By assessing and comparing the measurements provided by each unit with respect to the measurements provided by the other units and the data processed, the computing device determines whether any unit has been incorrectly arranged. When the computing device determines that such incorrect arrangement appears to exist, the motion tracking system is adjusted either digitally by the action of the computing device, or manually by the action of the person. For the latter, the computing device can inform the person or provide him/her with instructions on how the rearrange the unit(s) in accordance with the misplacement that the computing device has determined. The digital adjustment can involve: the modification of the correspondence between units and body members in the predetermined unit arrangement, in this way the measurements provided by each unit are assigned to the body members as determined by the computing device and not to the original predetermined unit arrangement (e.g. instead of considering a first unit to be arranged on the upper arm and a second unit arranged on the chest according to the original predetermined unit arrangement, the computing device considers that the first unit is arranged on the chest and the second unit is arranged on the upper arm after adjustment of the predetermined unit arrangement in this way); the swapping of measurements of a unit by those of another unit so that they likewise refer to the body member considered by the computing device; and/or the modification of the orientations measured by the concerned unit (e.g. instead of considering that a unit is providing a proper orientation measurement, the computing device digitally rotates the orientation measurement by an angular correction factor established based on the deemed incorrect orientation in the arrangement of the unit).

Measurements subsequent to the first sets of measurements can be modified in this manner, but also the first sets of measurements or measurements prior to the first sets (if any) can be processed again by the computing device and be digitally modified for establishing the orientation and motion of the tracked body members. The same occurs with the swapping of measurements or the modification of the predetermined unit arrangement, namely not only subsequent measurements are processed taking into account these changes but also the first sets of measurements or measurements prior to the first sets (if any) can be processed again by the computing device taking into account these changes.

Afterwards, the person may proceed to perform the second predetermined movement, which may be presented with the presenting means as well, so as to rehabilitate herself/himself without risk of injury that would be due to an incorrect arrangement of the IMUs resulting in an incorrect assessment of the physical exercise by the motion tracking system. The second predetermined movement is usually prescribed by a therapist for rehabilitation of the person.

The computing device assesses how accurately the person performs the second predetermined movement by comparing the motion sequence derived from the measurements with a set of predetermined movement constraints as known in the art, for example as described in commonly owned international application no. PCT/EP2019/066237, incorporated by reference in its entirety herein. The predetermined movement constraints may be set in the form of orientations, angular rotations, and/or accelerations that the body members must comply with. In this sense, the predetermined movement constraints impose, at least for each body member intended to move during the second predetermined movement and to have a unit arranged thereon according to the predetermined unit arrangement, one or more of:
- a predetermined movement orientation threshold or range;
- a predetermined movement motion threshold or range, relative to linear or angular motion; and
- a predetermined movement acceleration threshold or range.

The predetermined movement constraints preferably also includes any one of the above thresholds or ranges for body members expected to have a unit arranged thereon according to the predetermined unit arrangement even if they are not intended to move during the second predetermined movement, for example to check that the person does not incorrectly perform the movement because other body members are moved when they should not. By way of example, during a leg up movement, the ankle of the other leg should move little or nothing at all, therefore constraints to this end may be provided as well and measurements of a unit on said ankle or on the respective leg can be compared with these constraints for validation of the correct performance of the predetermined movement. Feedback about the performance of the movement is preferably provided to the person with presenting means so that the person knows how she/he is physically exercising and whether she/he must change the orientation and/or motion of any body member(s) to correctly perform the movement; also, the feedback may be digitally stored and even transmitted to another electronic device for analysis by a therapist.

The method does not require the provision of a template such as e.g. an image or a digital representation (i.e. casting of an optical image with a projector) on a surface that the person is required to arrange her/his limbs thereon for determining whether the IMUs having been arranged on the person according to the predetermined unit arrangement. The method does not require the solving of kinematic chain equations either for determining whether the IMUs having been arranged on the person according to the predetermined unit arrangement. Accordingly, the sets of measurements used for adjusting the operation of the motion tracking system can be provided during the actual motion tracking procedure.

In the context of the present disclosure, a predetermined movement comprises one or more movements involving linear motion or rotation of one or more body members; a plurality of movements may be, but is not necessarily, a repetition of a movement a number of times.

In some embodiments, the computing device digitally processes at least the second sets of measurements so as to further determine whether: any unit of the plurality of units is arranged on a body member of the person with an orientation outside of a predetermined orientation range for a unit on that body member; and/or two or more units of the plurality of units may be arranged on interchanged body members of the person according to the predetermined unit arrangement. In these embodiments, the method further comprises adjusting the operation of the motion tracking system when the computing device determines, based on at least the second sets of measurements, that: at least one unit has an orientation outside of the predetermined orientation range, and/or two or more units are arranged on interchanged body members.

The verification of the correct or incorrect arrangement of the IMUs may be also carried out while the person physically exercises by performing the second predetermined movement that is to fulfill the set of predetermined movement constraints (for the second predetermined movement). It may occur that the computing device does not detect (and, thus, does not determine) that one or more IMUs have been incorrectly arranged when the person was standing still and/or performing the first predetermined movement, but detects such situation while the person is performing the second predetermined movement. Then, the operation of the motion tracking system is to be adjusted when the computing device makes such determination upon processing the second sets of measurements. When the person then repeats the second predetermined movement or performs a different movement, the performance of said movement will be properly evaluated by the computing device thereby reducing the risk of an injury due to incorrect supervision and feedback.

The sequence of: performance of movement(s) by the person, measurements processing by the computing device for determining the existence of a possible problem, and adjustment of the operation of the motion tracking system, may be carried out a number of times as in a looped sequence so that the motion tracking system is continuously checking whether there is any problem in the motion tracking and adjusting the operation thereof for improving the quality of the physical rehabilitation.

In some of these embodiments, the operation of the motion tracking system is adjusted when the computing device determines, based on at least the second sets of measurements, that both: the person has not correctly performed the second predetermined movement due to measurements of particular one or more units not fulfilling the set of predetermined constraints for the second predetermined movement a predetermined number of times in a row, the particular one or more units being unit or units not supposed to move in the second predetermined movement; and the second set of measurements of the particular one or more units is indicative of a reduced motion (i.e. the motion is within a predetermined motion range) in each of these times (i.e. the attempts in which the person incorrectly performed the second predetermined movement in a row).

When the person performs a given movement several times in a row but the computing device considers that the movement is not correctly reproduced, the situation may sometimes be associated with an incorrect arrangement of the units. In particular, this is most likely the case when the particular one or more units are not to undergo linear motion or rotation (other than a minimal motion or rotation due to a non-perfect reproduction of movement) during the predetermined movement because said movement does not involve movement of the corresponding body member (or members), the measurements of this unit (or these units) are indicative of little or no motion/rotation (thereby fulfilling the criterion of no linear motion or rotation), yet the predetermined movement is determined as being incorrect due to an inadequate orientation of the unit or units each and every time for the predetermined number of times in a row. Said inadequate orientation in these attempts is indicative of an incorrect arrangement of the units that leads to an inaccurate posture evaluation since it is unlikely that the person will have an incorrect posture in all those attempts in a row, not to mention that the motion tracking system may provide feedback to the person so that she/he is aware of the offending body member and how the same should be oriented for the correct reproduction of the movement.

By way of example, the person is requested to rotate one or both arms upwardly while keeping the chest in an upright position. The person rotates the arm or arms and maintains the chest in the upright position as requested five times in a row, yet the motion tracking system informs the person that the chest thereof forms an angle between 20° and 30° with respect to the vertical in each of these five times. Such situation causes, in these embodiments, the determination that one or more IMUs have been incorrectly arranged.

In some embodiments, each unit of the plurality of units provides the first set of measurements of the person with the units arranged thereon performing the first predetermined movement, and the computing device digitally processes the first sets of measurements so as to further determine whether the person has performed the first predetermined movement according to a set of predetermined movement constraints for the first predetermined movement.

The first predetermined movement may be part of the physical exercise that the person is to do for rehabilitation purposes. Accordingly, the computing device is capable of detecting incorrect arrangement of the units on the body members during the rehabilitation of the tracked person. The computing device evaluates the movement performed by the person using the predetermined movements constraints for the first predetermined movement. Like with the second predetermined movement, which forms part of the physical exercise, the first predetermined movement has predetermined movement constraints at least for each body member intended to move during the first predetermined movement and to have a unit arranged thereon according to the predetermined unit arrangement, but preferably also have constraints for body members expected to have a unit arranged thereon according to the predetermined unit arrangement as well. These constraints can be one or more of: a predetermined movement orientation threshold or range; a predetermined movement motion threshold or range, relative to linear or angular motion; and a predetermined movement acceleration threshold or range.

In some of these embodiments, the operation of the motion tracking system is adjusted when the computing device determines, based on the first sets of measurements, that both: the person has not correctly performed the first predetermined movement due to measurements of particular one or more units not fulfilling the set of predetermined constraints for the first predetermined movement a predetermined number of times in a row, the particular one or more units being unit or units not supposed to move in the first predetermined movement; and the first set of measurements of the particular one or more units is indicative of a reduced motion in each of these times.

In some embodiments, the first predetermined movement is the same as the second predetermined movement.

In these embodiments, if the first predetermined movement is part of the exercises for the rehabilitation of the tracked person, the motion tracking system may continuously check and adjust the operation thereof based on the measurements provided by the plurality of units during rehabilitation of the person, namely, after arranging the plurality of units on the body members, the method is repeated one or a plurality of times, for instance it is repeated while the rehabilitation lasts.

In some embodiments, the method further comprises digitally providing, the computing device, a biomechanical model representing body members and joints of a person. Further, in these embodiments, the computing device digitally processes the first sets of measurements so as to further determine whether at least one body member of the person complies with one or more predetermined criteria set for the biomechanical model; and the operation of the motion tracking system is further adjusted when the computing device determines, based on at least the first sets of measurements, that at least one body member complies with any one of one or more predetermined criteria set for the biomechanical model.

The biomechanical model enables the validation of measurements provided by the IMUs because the measurements of the IMUs are, in principle, indicative of the orientation and motion of the tracked body members. The orientation and motion of the tracked body members may be simulated on the biomechanical model in accordance with the measurements.

The computing device modifies the biomechanical model using the measurements of the IMUs once processed, and determines whether any body member complies with a predetermined criterion or criteria, for example physical limitations of body members of a person as derived from the modified biomechanical model. When the computing device makes any such determination, it is considered that there is a problem in the motion tracking because it is not expected that the person will perform physically impossible or physically uncomfortable orientations or movements; namely, each criterion of the one or more predetermined criteria is indicative of an arrangement of at least one unit of the plurality of units not fulfilling the predetermined unit arrangement. This means that, in this case, the person may get injured because the computing device is or will not be, for some reason, adequately evaluating whether the person performs the second predetermined movement. Therefore, the supervision is not appropriate and the person may not be warned if the movement is incorrectly performed.

The operation of the motion tracking system is adjusted or further adjusted taking into account said compliance with any one of the one or more predetermined criteria set for the biomechanical model so as to properly evaluate the physical exercise of the person. The adjustment can comprise: the rearrangement of one or more units on the body members of the person so that the resulting arrangement fulfills the predetermined unit arrangement, and/or the modification of the biomechanical model such that body members and/or joints represented therein have orientations thereof adjusted or measurements of units swapped in order to more accurately represent the orientation and motion of the tracked body members. The adjustment of orientations in the biomechanical model entails applying an angular correction factor to the orientation measurements, the acceleration measurements or both of a unit. The swapping of measurements corrects the correspondence between units and body members in light of the fulfillment of the one or more predetermined criteria and the predetermined unit arrangement.

In some examples, the biomechanical model represents some body members and some joints of a person, said some body members at least including the body members to be tracked with the plurality of units and said some joints at least including the joints connected to the body members to be tracked with the plurality of units.

In some embodiments, the one or more predetermined criteria for the biomechanical model comprise that the at least one body member:

may have an orientation or may be moving following a motion that is not possible according to the biomechanical model;

may have an orientation during a first predetermined period of time that is uncomfortable according to the biomechanical model; and/or may have an orientation during a second predetermined period of time that according to the biomechanical model does not correspond to that of a person standing still or performing the first predetermined movement.

A number of predetermined thresholds is set for carrying out the determination of each of these criteria. By way of example, a predetermined threshold establishes when an orientation or motion is not possible, e.g. a hyperextension of the elbow. When the measurements of the IMUs are indicative of a hyperextension of the elbow, the computing device determines that there is a problem with the arrangement of the IMUs or with the biomechanical model. One or more first predetermined orientation thresholds or ranges are set to this end. The computing device compares orientation, linear or angular motion values resulting from the measurements of one or more units to check whether the criterion is met. For linear or angular motion, the computing device processes the orientation and/or acceleration measurements of a unit as known in the art to compute the linear or angular motion of the unit.

Similarly, one or more predetermined thresholds alongside the first predetermined period of time establish which orientations for given body members would be so uncomfortable that a person is unlikely to experience in a prolonged manner, for example. Whether an orientation is deemed uncomfortable can be initially established by way of tests carried out on people with different postures and orientations of body members and their reaction or pain in those cases, then one or more second predetermined orientation threshold(s) or range(s), e.g. predetermined deemed uncomfortable orientation threshold(s), can be made dependent upon the biomechanical model. This means that the threshold(s) or range(s) can vary in accordance with the biomechanical model and the measurements provided by the units because an orientation can be more or less uncomfortable depending on the orientations of other body member(s). The same is true for the criterion of the orientation of the body member(s) not corresponding to those expected for a person while standing still or performing the first predetermined movement. It may occur that the person is not standing in an upright position, or is performing a different predetermined movement, however when the assessment of the computing device indicates that said apparently incorrect orientation has been maintained for a considerable period of time (as set in the second predetermined period of time), it is considered that the person did comply with the standing still or first predetermined movement expected from her/him and the arrangement of the IMUs or the biomechanical model has a problem. Third one or more predetermined orientation thresholds or ranges can be set for establishing whether the criterion of the body member(s) not being oriented as expected for a person standing still or performing the first predetermined movement. It is noted that ranges can be set in one or more criteria, and the criteria being met when the values resulting from the measurements exceed one of the limits of the range but not the other one of the limits.

By way of example, a unit may be arranged on a body member such that the measurements thereof appear to be constantly biased towards one side (e.g. towards the front, towards the back, towards one lateral side) when represented on (i.e. applied to) and validated with the biomechanical model. That is to say, the orientation of the body member appears to be biased according to both the measurements and the biomechanical model. If such constant bias is of an amplitude that is considered to be very uncomfortable for the user to be constantly in, it is assumed and, thus, determined, that there is an error in the arrangement of the unit or units.

The computing device may preferably process measurements provided by the IMUs during a time span with a duration equal to or greater than the first or second predetermined period of time, that is to say, measurements corresponding to a plurality of time instants during the period of time have to be processed. In this way, the probability that the person really has the at least one body member in an uncomfortable orientation or has an orientation that does not correspond to that of a person standing still or performing the first predetermined movement is reduced.

In some embodiments, an adjustment of the operation of the motion tracking system, when the computing device determines that the at least one body member complies with any one of the one or more predetermined criteria set for the biomechanical model, comprises at least one of:

digitally modifying, the computing device, the biomechanical model based on at least the first sets of measurements;

providing a third set of measurements, by each unit of the plurality of units, of the person with the units arranged thereon performing a third predetermined movement, the third predetermined movement involving movement of each body member having a unit arranged thereon, and digitally modifying, the computing device, the biomechanical model based on at least the third sets of measurements; and rearranging two or more units of the plurality of units such that they are on other body members of the person.

The determinations made by the computing device that involve the use of the biomechanical model lead to digital modifications of the biomechanical model (the digital modifications include the possibility of digitally providing a new biomechanical model from scratch that replaces the former one), using the first sets of measurements resulting from the first predetermined movement of the person and, possibly, sets of measurements provided by the units earlier on, or using the third sets of measurements resulting from the third predetermined movement or movements of the person, which is a movement for calibrating the motion tracking system. Particularly, the calibration movement makes possible to digitally infer on which body member each IMU is arranged (i.e. a unit-to-body calibration), digitally modify an existing biomechanical model (or provide a new one) based on the measurements of the units, or both. A plurality of movements may be necessary for the computing device to be capable of inferring the IMUs arrangement and/or modifying the biomechanical model with a higher degree of certainty.

In order to rearrange the IMUs, the motion tracking system preferably provides (with presenting means) at least one user perceptible signal indicative of an incorrect arrangement of the two or more units. Depending on the measurements provided by the units and the movements performed by the person, the computing device is capable of determining on which body members the affected IMUs have been actually arranged, thus the motion tracking system may provide an instruction for rearranging the units that pinpoints each such IMU and indicates on which body member it should be arranged on.

In some embodiments, the computing device digitally modifies the biomechanical model based on at least the first sets of measurements when the computing device determines that the at least one body member may have an orientation or may be moving following a motion that is not possible according to the biomechanical model.

In some embodiments, each set of measurements processed by the computing device at least comprises an orientation of each respective unit.

The computing device uses these orientations when processing the measurements of the IMUs in order to determine how the tracked body members are oriented. And based on the orientations of the units (and, thus, of the body members), the computing device determines whether two or more IMUs have been arranged on interchanged body members, any IMU has been arranged tilted or upside-down on a body member. Also, in the embodiments in which the biomechanical model is provided, the computing device uses the orientations to detect body members moving in a manner that appears to be impossible, and body members having an uncomfortable or impossible orientation.

In some embodiments, the computing device digitally computes angles formed between the orientations and a common direction or plane, the common direction or plane preferably being a vertical direction or a vertical plane.

By computing angles between each orientation and a common direction or plane the computing device may digitally infer and, thus, determine the existence of incorrect arrangement of the IMUs. In some cases, the computing device determines that one or more units are arranged on body members of the person with an orientation not fulfilling the predetermined position and orientation constraints if the computed angle is outside of a predetermined angle range for a unit on a given body member.

In some of these embodiments, the common direction or plane is a vertical direction or a vertical plane. The angles computed are indicative of vertical inclination of the IMUs and, thus, of the body members.

By way of example, when an IMU is arranged on a chest and the person is standing still or performing a movement involving little or no motion of the chest, a vertical inclination within the range of e.g. 30° up to 90° (namely, the vertical inclination is outside of the ranges 90° to 180° and 0° to 30°) reveals an incorrect arrangement of the IMU on the chest, or that the IMU to be arranged on the chest has been arranged on a different body member.

In some other embodiments, the common direction or plane is a vertical plane preferably being a coronal plane; in these embodiments, the orientations are projected onto said plane, and the computing device computes the angles formed between the projected orientations and a common direction contained in said plane. The angles computed are indicative of an inclination with respect to the common direction of the IMUs, and thus, of the body members; by way of example, if the common direction is a vertical direction within the plane, the angles are indicative of lateral inclination of the IMUs.

In some embodiments, the method further comprises providing a set of calibration measurements, by each unit of the plurality of units, of the person with the units arranged thereon performing a predetermined calibration movement, the predetermined calibration movement involving movement of each body member having a unit arranged thereon, and digitally determining, the computing device based on the sets of calibration measurements, on which body member of the person each unit may be arranged according to the predetermined unit arrangement.

The predetermined calibration movement enables the computing device to establish a unit-to-body calibration, that is to say, identify which unit is arranged on each body member based on the sets of calibration measurements. Accordingly, even if the person inadvertently swapped two or more units, the computing device will detect it owing to said measurements. Moreover, in some of these embodiments, the computing device not only establishes on which body member each unit is but also the orientation thereof. This may be achieved by considering the particularities of the calibration movement to be performed, the measurements themselves and the typical physical limitations of people that cannot move body members or rotate the same around joints beyond certain orientations or angles. A biomechanical model may assist in such determination in those embodiments in which the same is provided. Accordingly, the computing device processes the sets of calibration measurements and compares the orientations and/or movement of the units with some predetermined movement constraints related to the predetermined calibration movement, either with the aid of the biomechanical model or not. The predetermined movement constraints may include, at least for each body member intended to move during the predetermined calibration movement and to have a unit arranged thereon according to the predetermined unit arrangement (but preferably also for other body members that are to have a unit arranged thereon according to the predetermined unit arrangement but which are to move a reduced amount or remain motionless), one or more of: a predetermined calibration movement orientation threshold or range; a predetermined calibration movement motion threshold or range, relative to linear or angular motion; and a predetermined calibration movement acceleration threshold or range.

In some embodiments, the method further comprises arranging a strap of each unit of the plurality of units on the different body member of the person, the units of the plurality of units being arranged on the different body members by attaching to the respective strap, providing a signal or data packet by each unit of the plurality of units corresponding to an electric coupling between the unit and the respective strap, and digitally determining, the computing device, on which body member of the person each unit may be arranged based on the signals or data packets and according to the predetermined unit arrangement.

The electric coupling of units with straps provides a unique electric response within the motion tracking system that makes possible to identify which unit has been attached to a given strap. To this end, each strap is provided with an electric component, preferably a passive component, providing a different electric response upon completion of the electric circuit, which occurs by the coupling of the unit therewith. For example, the electric components are resistors with different resistance. The voltage or current resulting from the electric circuit is transmitted from the unit to the computing device in the form of a signal, or in the form of a data packet, in which case the unit generates the data packet with an identifier based upon the electric response.

In some embodiments, the method further comprises, prior to the step of arranging each unit of the plurality of units on the different body member of the person, providing at least one user perceptible signal indicative of the predetermined unit arrangement and/or at least one user perceptible signal indicative of an instruction to arrange the plurality of units according to the predetermined unit arrangement.

In some embodiments, an adjustment of the operation of the motion tracking system, when the computing device determines that at least one unit has an orientation outside of the predetermined orientation range and/or two or more units are arranged on interchanged body members, comprises at least one of:

digitally modifying, the computing device, the predetermined unit arrangement;

digitally rotating 180°, the computing device, the measurements provided by one or more units of the plurality of units to account for units arranged upside-down with respect to the predetermined unit arrangement;

rearranging the at least one unit having the orientation outside of the predetermined orientation range such that at least one unit is arranged on the same body member but in a different position thereof and/or with a different orientation; and rearranging the two or more units of the plurality of units such that they are on other body members of the person.

The digital modification of the predetermined unit arrangement may entail changing the unit to body member correspondence, or maintaining the original correspondence but swapping the measurements of two or more units so that the measurements actually refer to the expected body members. To this end, the computing device either uses the first sets of measurements for performing the digital modification, or requests the user to perform a predetermined calibration movement so that the corresponding sets of measurements provided by the plurality of units are used by the computing device in the digital modification of the predetermined unit arrangement.

The digital rotation by 180° of the measurements of the unit(s) solves the problem of the unit(s) being arranged upside-down. Hence, if the person arranged one or more units with the one side thereof (e.g. the bottom part) substantially oriented towards the opposite direction with respect to predetermined position and orientation constraints set in the computing device, the computing device digitally flips the measurements so that the result is as if the units had been properly oriented aside from tolerances due to imperfect arrangements. The person may also be informed of the unit(s) being placed upside-down, so the person is able to rearrange the unit(s) in some other embodiments instead of virtually flipping the measurements.

In order to rearrange the IMUs, the motion tracking system may provide (with presenting means) at least one user perceptible signal indicative of an incorrect arrangement of the two or more units and/or at least one user perceptible signal indicative of an instruction to rearrange the two or more units.

In some of these embodiments, the adjustment of the operation of the motion tracking system comprises halting a motion tracking procedure with the motion tracking system until the two or more units of the plurality of units have been rearranged.

In some embodiments, first, second and third units of the plurality of units are respectively arranged on: a chest, an upper arm and a lower arm. In some embodiments, first, second, third, fourth and fifth units of the plurality of units are respectively arranged on: a chest, a right upper leg, a right lower leg, a left upper leg and a left lower leg. In some embodiments, first and second units of the plurality of units are respectively arranged on: an upper back and a lower back. In some embodiments, first and second units of the plurality of units are respectively arranged on: a chest and a forehead.

In some embodiments, each unit of the plurality of units comprises at least one of: an accelerometer, a gyroscope and a magnetometer. In some of these embodiments, each unit of the plurality of units comprises an accelerometer and a gyroscope. In some of these embodiments, each unit of the plurality of units further comprises a magnetometer.

A second aspect of the disclosure relates to a motion tracking system comprising:

a computing device comprising at least one processor and at least one memory, the at least one processor being configured, together with the at least one memory, to carry out digital steps of a method according to the first aspect of the disclosure; and a plurality of inertial measurement units adapted to be arranged on body members of the person.

The motion tracking system allows a person to improve her/his physical condition by means of physical exercises without requiring the presence of a therapist. Furthermore, the system is capable of detecting possible incorrect arrangements of the IMUs thereof on the body members of the tracked person; to this end, the at least one processor of the computing device digitally processes the measurements provided by the IMUs while the person is standing still or performing predetermined movements, the latter including, in preferred embodiments, predetermined movement or movements of the physical exercise for rehabilitation of the person. Said movement or movements of the physical exercise is/are preferably prescribed by a therapist supervising the physical condition and rehabilitation of the person.

In some embodiments, the motion tracking system further comprises presenting means (e.g. a screen, audio output means such as loudspeakers, a vibrating device, etc.).

In some embodiments, the motion tracking system is communicatively coupled with presenting means.

A third aspect of the disclosure relates to a computer program product that has instructions which, when executed by a computing device of a motion tracking system comprising a plurality of inertial measurement units adapted to be arranged on body members of the person, cause the computing device to perform the digital steps of a method according to the first aspect of the disclosure.

Upon running the computer program product on one or more processors of the computing device, the motion tracking system both detects whether the IMUs of the system may have been incorrectly arranged on the person, and supervises the movements performed by the person as part of her/his physical exercises for rehabilitation or improvement of the physical condition. The computer program product may also command the provision of feedback related to the physical exercises so that the person and/or the therapist are informed about the activity of the tracked person.

In some embodiments, the computer program product is embodied on a non-transitory computer readable medium.

A fourth aspect of the disclosure relates to a data stream which is representative of a computer program product according to the third aspect of the disclosure.

Same advantages as those described for the first aspect of the disclosure also apply to the second, third and fourth aspects of the disclosure.

BRIEF DESCRIPTION OF THE DRAWINGS

To complete the description and in order to provide for a better understanding of the disclosure, a set of drawings is provided. Said drawings form an integral part of the description and illustrate embodiments of the disclosure, which should not be interpreted as restricting the scope of the disclosure, but just as examples of how the disclosure can be carried out. The drawings comprise the following figures.

DETAILED DESCRIPTION OF THE DRAWINGS

Figure 1:
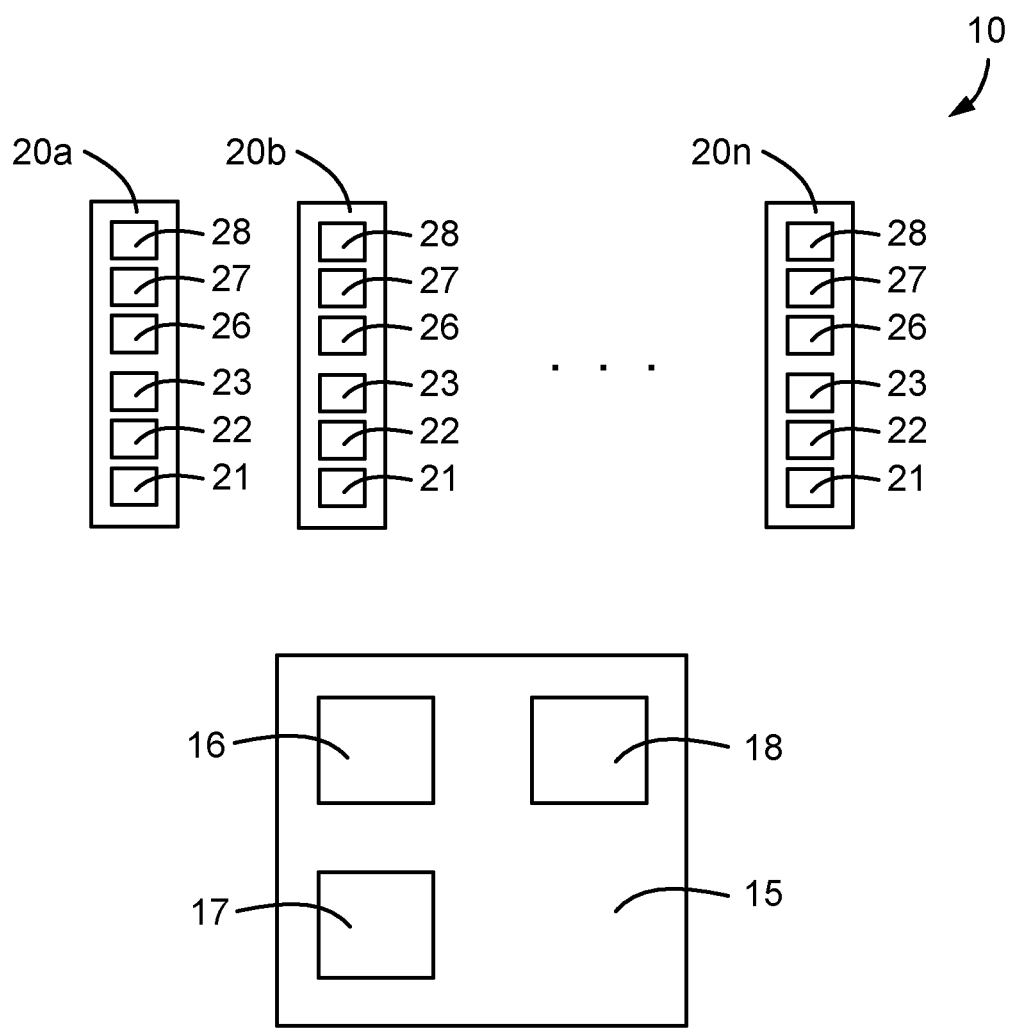
FIG. 1 diagrammatically shows a motion tracking system in accordance with an embodiment.

FIG. 1 diagrammatically shows a motion tracking system 10 in accordance with an embodiment. The motion tracking system 10 includes a plurality of inertial measurement units 20a-20n, and a computing device 15.

Each IMU 20a-20n includes one or more sensing devices selected from: an accelerometer 21, a gyroscope 22 and a magnetometer 23. In the embodiment of FIG. 1, each IMU 20a-20n includes all three sensing devices. Preferably, all IMUs 20a-20n include the same sensing devices.

The IMUs 20a-20n further include at least one processor 26, at least one memory 27, and a first communications module 28 for transmitting and receiving data that enables the IMUs to transmit (through a wired or wireless communications technology and protocol known by a skilled person, for instance but without limitation, Bluetooth communications, cellular network communications such as GSM, UMTS or LTE, wireless LAN communications, etc.) measurements of the sensing device(s) 21-23 to the computing device 15. The same first communications modules 28 enable the units 20a-20n to receive data from the computing device 15.

In some preferred embodiments, the at least one processor 26 of the IMUs 20a-20n runs a sensor fusion algorithm for processing the measurements of the sensing devices 21-23 within the respective IMU. The sensor fusion algorithm is intended to enhance the raw measurements of the sensing devices by correcting errors thereof due to drifts of the sensing devices and, thus, outputs processed measurements that are to be transmitted to the computing device 15.

The computing device 15 includes at least one processor 16, at least one memory 17, and a second communications module 18 for transmitting and receiving data.

The computing device 15 is capable of storing, in the at least one memory 17, predetermined unit arrangements, predetermined position and orientation constraints, predetermined movements and predetermined movement constraints associated therewith, feedback generated while a tracked person physically exercises, etc. Any of these data can be transmitted to and/or received from another electronic device thanks to the second communications module 18. For example, a therapist is able to receive the feedback at a computing device in a hospital so as to monitor the evolution of the person. Based on the feedback received, the therapist is able to adjust the difficulty of the predetermined movement(s), the number of repetitions thereof, prescribe new predetermined movements, etc. so that the person may further exercise using the motion tracking system.

FIGS. 2A to 2D show a person 1 standing still with IMUs 20a-20e of a motion tracking system arranged thereon. The predetermined unit arrangement in each of these cases indicates on which body members the IMUs shall be arranged on.

Figure 2A:
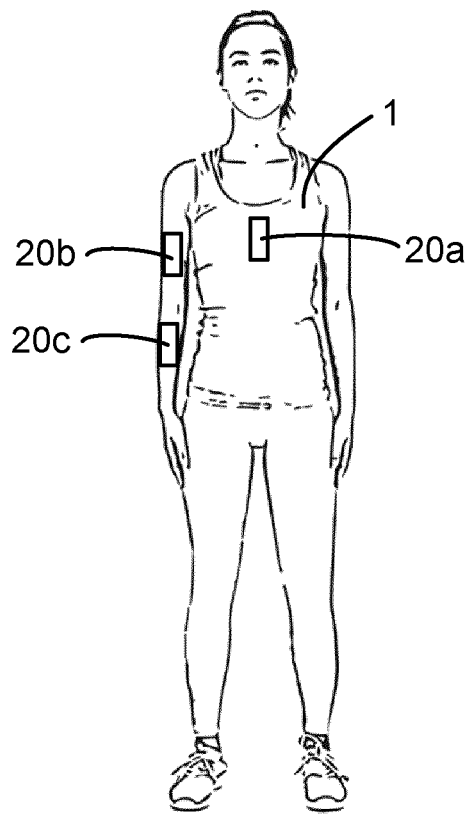
FIGS. 2A to 2D show a person standing still with IMUs of a motion tracking system arranged thereon.

In the example of FIG. 2A, the person 1 has a first IMU 20a attached to the chest, a second IMU 20b attached to an upper arm, and a third IMU 20c attached to a lower arm of the same arm, in this case the right arm.

Figure 2B:
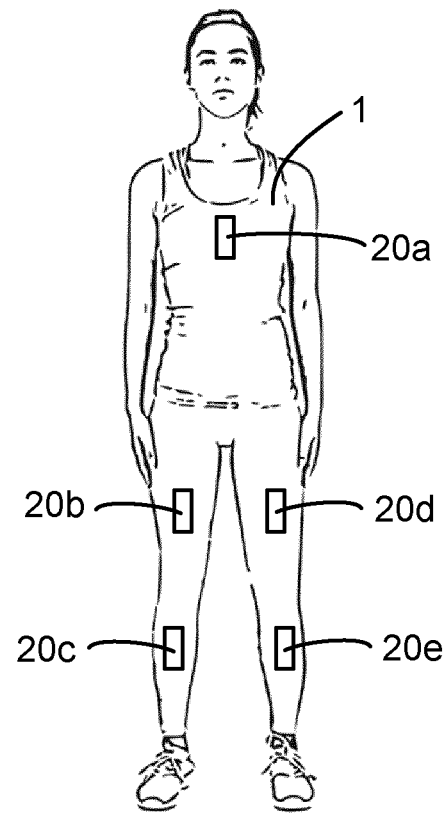

In the example of FIG. 2B, the person 1 has the first IMU 20a attached to the chest, the second IMU 20b attached to the right thigh, the third IMU 20c attached to the right shin, a fourth IMU 20d attached to the left thigh, and a fifth IMU 20e attached to the left shin.

Figure 2C:
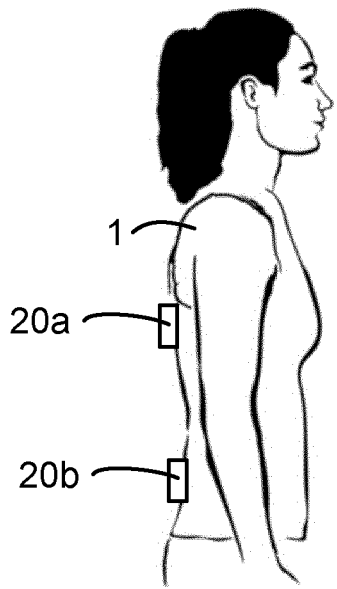

In the example of FIG. 2C, the person 1 has the first IMU 20a attached to the upper back and the second IMU 20b attached to the lower back.

Figure 2D:
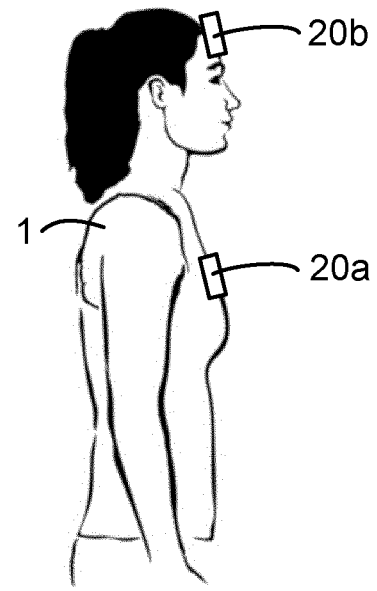

In the example of FIG. 2D, the person 1 has the first IMU 20a attached to the chest and the second IMU 20b attached to the forehead.

Figure 3A:
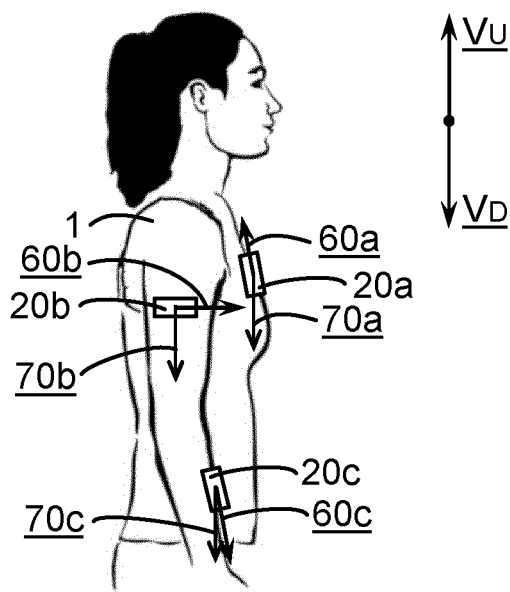
FIGS. 3A and 3B show a person standing still with IMUs of a motion tracking system incorrectly arranged thereon.
Figure 3B:
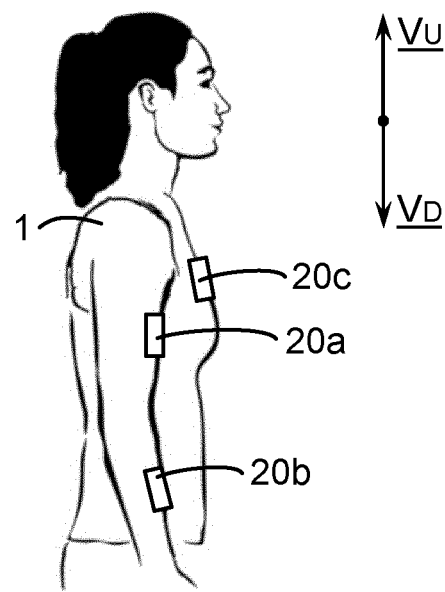

FIGS. 3A and 3B show a person 1 standing still with IMUs 20a-20c of a motion tracking system incorrectly arranged thereon.

In the example of FIG. 3A, the person 1 has arranged the first IMU 20a on the chest, the second IMU 20b on the right upper arm, and the third IMU 20c on the right lower arm. For each of the IMUs 20a-20c, the corresponding unit axis 60a-60c pointing towards the bottom part thereof has been represented with an arrow for illustrative purposes; in this example, these unit axes 60a-60c also correspond to longitudinal axes of the units 20a-20c, but in other embodiments they may correspond to widthwise axes of the units 20a-20c for example. There is also illustrated, in the form of arrows, the gravity acceleration 70a-70c as measured by the accelerometer of each of the units 20a-20c.

As it can be appreciated, the second IMU 20b has been arranged on a side of the right upper arm and with the bottom part of the unit facing towards the front-facing direction of the person. Accordingly, the gravity acceleration 70b measured by said unit 20b is not substantially aligned with the bottom part of the unit, i.e. the unit is not facing downwards vertically, thereby existing an error in the orientation of the unit that may result in incorrect motion tracking.

The computing device of a motion tracking system is capable of determining this error in the arrangement of the second unit 20b owing to the measurements provided by the same while the person is standing still or performing a predetermined movement that involves the movement (a linear motion and/or a rotation) of at least the right upper arm. In this case, the motion tracking system is to have its operation adjusted by requesting the person 1 to rearrange the unit on the arm such that the bottom side thereof is facing vertically and downwards and substantially aligned with the gravity acceleration 70b measured.

If predetermined position and orientation constraints related to this predetermined unit arrangement indicate that the second IMU 20b is to be arranged on the front-facing part of the right upper arm, when the person performs a predetermined movement the computing device is capable of determining that, in addition to not being correctly oriented, the unit 20b is not correctly positioned either. If this is determined by the computing system, the motion tracking system requests the person 1 to rearranged the unit on the right upper arm such that it is on the front part of the right upper arm rather than on the side thereof.

The third IMU 20c has the unit axis 60c substantially pointing downwards while the person 1 is standing still with the right arm running parallel to the body. The angle difference between the gravity acceleration 70c measured and the unit axis 60c may be accepted for the motion tracking procedure if it does not exceed a predetermined threshold set in the computing device, which is configurable for a more or less accurate assessment of correct reproduction of movements by the tracked person 1.

Concerning the first IMU 20a, the unit axis 60a thereof is substantially upside-down with respect to the gravity acceleration 70a measured. The computing device determines that this unit has an orientation outside of a predetermined orientation range (e.g. 20° towards either side from a vertical downwards direction as represented with the $V_D$ vector for clarity purposes only) and, thus, the operation of the motion tracking system is to be adjusted, for instance by digitally flipping the measurements, or by requesting the person to flip 180° the first IMU 20a.

In the example of FIG. 3B, the person 1 has arranged the first IMU 20a on the right upper arm, the second IMU 20b on the right lower arm, and the third IMU 20c on the chest. The IMUs 20a-20c are attached to the body members in the correct position and with the correct orientation according to the predetermined position and orientation constraints for this predetermined unit arrangement. However, the predetermined unit arrangement set in the computing device has the following correspondence: the first IMU 20a is to be on the chest, the second IMU 20b is to be on the right upper arm, and the third IMU 20c is to be on the right lower arm. Therefore, the current arrangement of units 20a-20c does not match this unit to body member correspondence.

When the person 1 performs a predetermined movement involving motion of at least two of these body members, or two predetermined movements each involving motion of one different body member of these three, the computing device determines that the units are incorrectly arranged. For example, if the person 1 raises the right arm, the unit 20a that was supposed to be on the chest should provide measurements indicative of little or no movement at all, yet in this case that unit 20a has been arranged on the right upper arm, thus the measurements are indicative of a significant rotation. In contrast, the units 20b, 20c that were supposed to be on the upper and lower arm, respectively, should provide measurements indicative of a significant rotation, yet in this case the third unit 20c provides measurements indicative of little or no movement at all.

The computing derives that at least the first and third units 20a, 20c have not been correctly arranged in accordance with the predetermined unit arrangement. The motion tracking system may request the person 1 to at least rearrange these units; alternatively, the computing device may trigger a new unit to body member calibration by requesting the person to keep the units arranged as they are and perform one or more predetermined calibration movements for inferring on which body member each unit is arranged. Or, in another embodiment, the computing device may digitally modify the predetermined unit arrangement such that it has the following correspondence: the first IMU 20a is on the right lower arm, the second IMU 20b is on the right upper arm, and the third IMU 20c is on the chest; the same may also be accomplished by digitally swapping the measurements of the first unit 20a by those of the third unit 20c.

If the person 1 rearranges these two units 20a, 20c or the computing device modifies the predetermined unit arrangement, there is still a problem in the unit arrangement since the computing device considers that the second IMU 20b is on the upper arm rather than on the lower arm, and the first IMU 20a is on the lower arm rather than on the upper arm. Upon performing another predetermined movement, for instance a flexion whereby only the lower arm raises, the computing device digitally processes the sets of measurements provided by each of the units 20a-20c and detects that the measurements of the first IMU 20a and the third IMU 20c are indicative of little or no movement, whereas the measurements of the second IMU 20b are indicative of a significant rotation when it was supposed to be (almost) motionless.

From these measurements and the previous measurements, the computing device derives that the first and second IMUs 20a, 20b are on interchanged body members, and so the operation of the motion tracking system is to be adjusted in the same manner as before.

A non-exhaustive list of examples of incorrect IMU arrangements is now described.

Other Examples Related to the Exemplary Arrangement of FIG. 2A a) It may be determined that there is a problem in the arrangement of one or more units when a vertical inclination of the IMU arranged on the chest is greater than 110° and smaller than 160° during a time in which the person 1 is expected to be in a lying resting position while performing one or more predetermined movements that does or do not involve considerable movement of the chest. While the person is lying and performing the movement(s), the chest of the person 1 is expected to be substantially parallel to the surface on which the person is lying, thus a vertical inclination being within the aforementioned range is indicative of the chest not being substantially parallel, therefore it is concluded that there is an incorrect arrangement of IMU(s).

Figure 4:
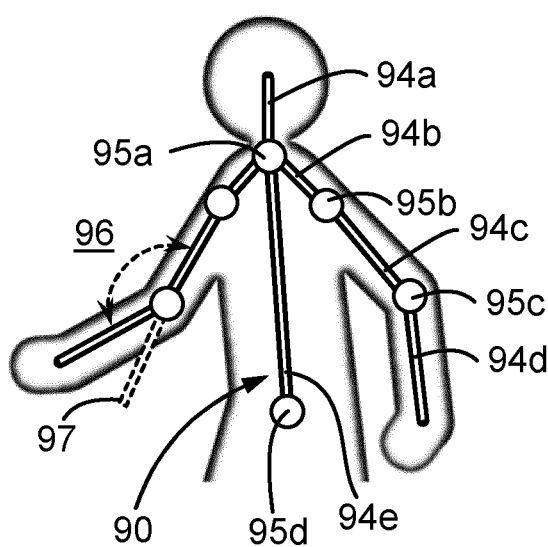
FIGS. 4 and 5 show diagrammatical representations of biomechanical models.

The vertical inclination is measured as the angle formed between a vector representing the orientation of the segment of the body member (for example, with reference to the lower arm represented in FIG. 3A, the orientation of the segment thereof corresponds to vector 60c) and a vector corresponding to a vertical direction, for instance the vector $V_U$ represented in FIGS. 3A and 3B (or the vector $V_D$, but it is noted that the selection of one or the other vector may result in a different angular value, thus the predetermined threshold or thresholds may have to be adjusted based on the vector used). In the context of the above and the following examples described herein, the vector $V_U$ is used for defining the vertical inclination and the predetermined thresholds associated therewith.

b) It may be determined that there is a problem in the arrangement of one or more units when the vertical inclination (or an average vertical inclination, i.e. a weighted sum of a set of vertical inclination samples) of the IMU arranged on the chest is such that the inclination currently computed is greater than a predetermined maximum vertical inclination set in the computing device for the performance of a particular movement, and additionally the vertical inclination as computed from the measurements of said IMU did not become smaller than said predetermined maximum vertical inclination after a predetermined period of time (e.g. 15 seconds, 20 seconds, 30 seconds, etc.) has elapsed. In such situation, the person is expected to correct the orientation of the chest towards a less demanding orientation which, in turn, would reduce the resulting vertical inclination; if the vertical inclination does not go below the predetermined maximum, usually there is a problem in the arrangement of IMUs.

c) It may be determined that there is a problem in the arrangement of one or more units when the units are placed in such a way that the digitally provided biomechanical model (for example a biomechanical model as represented in FIG. 4 below) indicates a hyperextension of the elbow, which is a movement that most people cannot perform without getting injured.

Examples Related to the Exemplary Arrangement of FIG. 2B d) It may be determined that there is a problem in the arrangement of one or more units when the vertical inclination of any of the IMUs is larger than 90° when assuming an upright standing posture (e.g. while the person 1 is to be standing still for instance before performing a movement).

e) It may be determined that there is a problem in the arrangement of one or more units when the lateral inclination of the IMU arranged on the chest is larger than 60° in an upright standing position or during performance of movements that do not require significant movement of the chest.

The lateral inclination is measured as the angle formed between a vector representing the projection of the orientation of the segment of the body member (for example, with reference the lower arm represented in FIG. 3A, the orientation of the segment thereof corresponds to vector 60*c*) onto a plane such as the coronal plane, and a vector that may correspond to a vertical direction on said plane (said vector corresponding to the vertical direction on the plane may also correspond to, for instance, the vector $V_U$ represented in FIGS. 3A and 3B, or the vector $V_D$). In the above example, the vector $V_U$ comprised in the coronal plane is used for defining the lateral inclination and the predetermined thresholds associated therewith.

f) It may be determined that there is a problem in the arrangement of one or more units when the vertical inclination of the IMU arranged on the chest or the IMU arranged on any of the lower legs is larger than 90° when the person 1 is to be in a sitting position.

Examples Related to the Exemplary Arrangement of FIG. 2C g) It may be determined that there is a problem in the arrangement of one or more units when the vertical inclination (or an average vertical inclination) of any IMU is larger than 20° but smaller than 90° when it is assumed that the person 1 is to be in an upright standing position.

h) It may be determined that there is a problem in the arrangement of one or more units when the IMU arranged on the lower back has significantly more lateral inclination (e.g. more than 15°) than the IMU arranged on the upper back sensor during performance of movements such as bending the trunk to the side.

Examples Related to the Exemplary Arrangement of FIG. 2D i) It may be determined that there is a problem in the arrangement of one or more units when the digitally provided biomechanical model shows both neck extension and neck bending of 90° or more.

j) It may be determined that there is a problem in the arrangement of one or more units when the vertical inclination of the IMU arranged on the chest, while it is assumed that the person 1 is in an upright standing position, is such that the inclination currently computed is greater than a predetermined maximum vertical inclination set in the computing device for the performance of a particular movement, and additionally the vertical inclination as computed from the measurements of said IMU did not become smaller than said predetermined maximum vertical inclination after a predetermined period of time (e.g. 15 seconds, 20 seconds, 30 seconds, etc.) has elapsed.

FIG. 4 shows a diagrammatical representation of a biomechanical model 90.

The biomechanical model 90 represents part or the entirety of a person in terms of segments 94*a*-94*e* of body members (illustrated with straight lines) and joints 95*a*-95*d* connecting the same.

The biomechanical model 90 is digitally provided based on the measurements provided by each IMU of the motion tracking system and the predetermined unit arrangement, also taking into account any predetermined position and orientation constraints that may have been defined. The biomechanical model 90 is modified based upon the measurements processed by the computing device so as to represent how the body members of the person are positioned and oriented, and how the body members move. Accordingly, the biomechanical model 90 reproduces the behavior of the person in accordance with the measurements and makes possible to establish whether one or more predetermined criteria related to possible incorrect IMU arrangements are fulfilled as the biomechanical model 90 reproduces the orientations and movements of the body members.

Each joint 95*a*-95*d* of the biomechanical model 90 has one or more predetermined thresholds associated therewith defining at least one of:
 which angular relationships between the body members connected therewith are considered as being impossible for a person,
 which angular relationships between the body members connected therewith are considered as being uncomfortable for a person, and
 which motion between the body members connected therewith are considered as being impossible for a person.

The angular relationships may be defined in a number of ways that ultimately represent the orientation of body members relative to other body members.

By way of example, the angular relationship 96 between a lower arm and an upper arm is considered to be normal within the range of 5° up to 180°. At 180°, the lower arm would be parallel to the upper arm (in the position of the model 90 illustrated in FIG. 4 the lower arm would coincide with the dashed footprint 97). An angular relationship between said two same body members is considered to be uncomfortable for a person within the range of 180° up to 190° due to a hyperextension of the elbow, whereas it is considered to be impossible (without getting injured) for angles above 190°.

Figure 5:
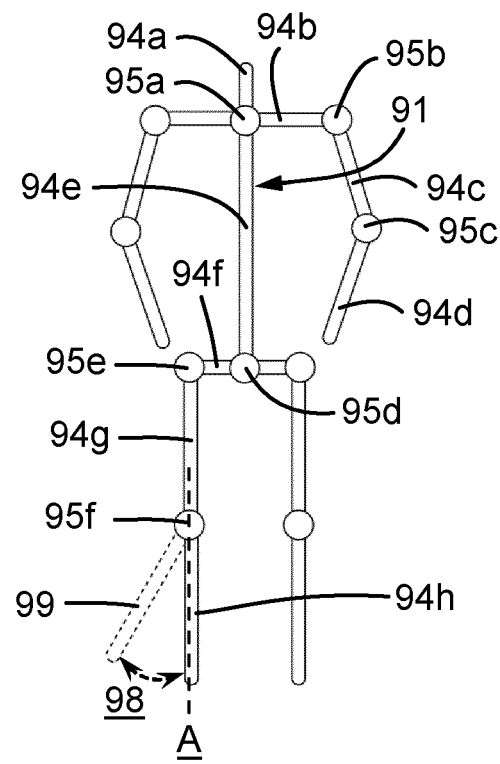

FIG. 5 shows a diagrammatical representation of another biomechanical model 91 representing body members 94*a*-94*h* and joints 95*a*-95*f*.

In this example, the biomechanical model 91 is used for the evaluation of a movement involving the legs of a tracked person. In the current position (in which the body members are represented with solid lines), the measurements as applied to the biomechanical model 91 do not comply with any predetermined criterion corresponding to body members: having an orientation or moving following a motion that is not possible, having an orientation during a predetermined period of time that is considered uncomfortable for a person, and having an orientation during a predetermined period of time that is considered as not corresponding to that of a person standing still or performing a given predetermined movement.

However, if the measurements provided by the units, once applied to the biomechanical model 91, resulted in the orientation of the right shin being in the dashed footprint 99 and contained in the coronal plane (i.e. the right shin is laterally rotated), the motion tracking system would determine that there is an incorrect arrangement of the units since that orientation of the shin is impossible according to the biomechanical model 91. The angle 98, in this case, is defined with respect to the axis A (represented with a dashed line) of the segment 94g of the thigh, and an acceptable range for said angle 98 is $-3°$ to $3°$ (i.e. $3°$ to either side of the axis A), so in this case the angle 98 is excessive resulting in an impossible orientation. In other embodiments, the angle 98 is defined around the joint 95g, for example, in which the case the acceptable angular range is $177°$ to $183°$. These angular ranges are defined with respect to the impossible, lateral rotation of the shin, therefore the common bending of the knee is not determined as an impossible orientation or motion of the upper and lower leg because the lower leg would have an orientation within the acceptable angular range.

Figure 6:
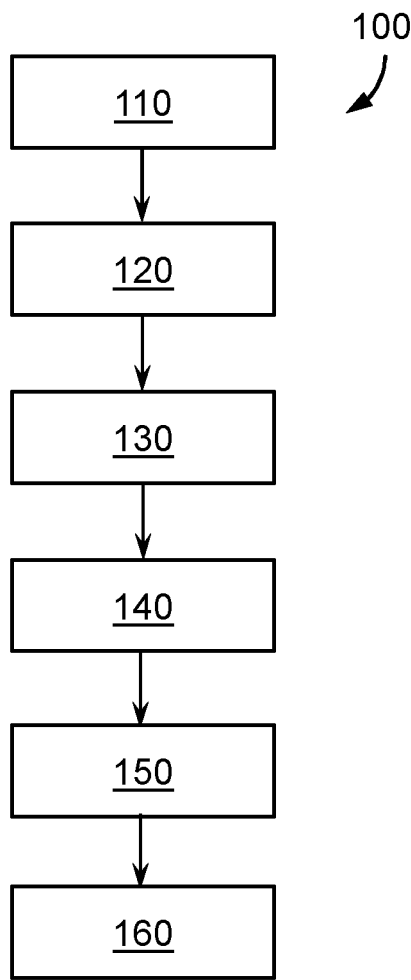
FIGS. 6 to 8 diagrammatically show methods for the physical exercising of a person with a motion tracking system in accordance with embodiments.

FIG. 6 diagrammatically shows a method 100 in accordance with an embodiment.

The method 100 comprises a step of arranging 110 each inertial measurement unit of a plurality of units of a motion tracking system on a different body member of a person according to a predetermined unit arrangement. A predetermined unit arrangement may be, for instance, any one of those described with reference to FIGS. 2A to 2D.

By way of example, the person whose motion is to be tracked attaches the three IMUs of a motion tracking system on a chest, right upper arm and right lower arm as defined in the predetermined unit arrangement. In an ideal situation, when a computing device of the motion tracking system already has a predetermined unit arrangement defining the correspondence between each IMU and a particular body member, the person attaches each of the IMUs on the body members fulfilling this correspondence, but the person may inadvertently swap some or all IMUs, and/or position or orient them inadequately with respect to predetermined position and orientation constraints associated with the predetermined unit arrangement that the computing device is provided with. With the method 100 it is possible to deal with such problems.

In some embodiments, the predetermined unit arrangement of the computing device does not include a correspondence between IMUs and body members until the person has performed a unit-to-body calibration. That is to say, the person arranges 110 the IMUs on the particular body members as defined in the predetermined unit arrangement; then, the person performs a predetermined calibration movement so that the computing device may determine on which body member each particular IMU has been arranged and, preferably, also with which orientation each particular IMU has been arranged on the body members.

The method 100 further comprises a subsequent step in which each unit of the motion tracking system provides 120 a first set of measurements of the tracked person (while the person has the units arranged 110 on the body members) standing still and/or performing a first predetermined movement that involves motion of one or more body members with a unit arranged thereon. In some cases, the person stands still during one or more periods of time and performs the first predetermined movement during one or more other periods of time. The measurements of the first sets of measurements may be raw measurements, i.e. values measured by the corresponding sensing device, or processed measurements, i.e. values modified by the processor(s) of the IMUs, for instance owing to a sensor fusion algorithm that is intended to improve the measurements of the IMU by combining the measurements of the different sensing devices.

The first set of measurements of each unit is provided to the computing device for digital processing 130 thereof. The sets of measurements are preferably wirelessly transmitted to the computing device.

The computing device processes 130 the measurements (and, possibly but not necessarily, some other previous measurements provided by the IMUs while tracking the person) and determines whether any IMU is arranged on a body member of the person with an orientation outside of a predetermined orientation range for a unit on that body member. Therefore, measurements of a unit that is to be arranged on the chest, for example, are not supposed to indicate that the unit has a tilted orientation or an upside-down orientation when the person is e.g. in an upright position, either standing still or performing a predetermined movement, or has a vertical orientation (e.g. parallel or substantially parallel to a vector such as vector $V_D$ or $V_U$ as illustrated in FIGS. 3A and 3B) when the person is e.g. lying on the floor. This determination may be made with the orientations provided by the units or with orientations processed by the computing device. For example, the computing device may transform the orientations to a different frame of reference and/or compute angles formed between a given orientation and a reference direction or plane, including first projecting the orientation onto a particular reference plane and then computing the angle formed between the orientation as projected onto the plane and a particular direction.

Additionally or alternatively, as part of the digital processing 130 the computing device determines whether two or more IMUs may have been arranged on interchanged body members of the person based on the predetermined unit arrangement, thereby not fulfilling the unit to body member correspondence. For example, when the person is to perform a first predetermined movement corresponding to a rotation of the right arm from a vertical orientation thereof to a horizontal orientation thereof, the first sets of measurements shall reveal this rotation for the right upper arm and right lower arm units, and little or no rotation of the chest unit. If the measurements reveal a similar rotation for the right lower arm and the chest units, and no rotation for the right upper arm, it is determined that the right upper arm and chest units have been interchanged.

Also, in some embodiments, the computing device may determine, as part of the digital processing 130, whether at least one body member of the person is in compliance with one or more predetermined criteria set for a biomechanical model digitally provided, for example that the at least one body member: may have an orientation or may be moving following a motion that is not possible according to the biomechanical model; may have an orientation during a first predetermined period of time that is uncomfortable according to the biomechanical model; and/or may have an orientation during a second predetermined period of time that according to the biomechanical model does not correspond to that of a person standing still or performing the first predetermined movement. In these embodiments, the computing device previously digitally provides the biomechanical model of a person, for example it generates one, or retrieves one from a memory thereof or an electronic device. The computing device applies the measurements provided by the units to the biomechanical model so that the same is modified in accordance with the measurements.

In some embodiments, the first predetermined movement is part of the physical exercise that the person is to perform for rehabilitation purposes. In these embodiments, as part of the digital processing 130, the computing device also determines whether the person has performed the first predetermined movement according to a set of predetermined movement constraints for the first predetermined movement.

The method 100 further comprises the subsequent step of adjusting 140 the operation of the motion tracking system when the computing device has made any such determination while digitally processing 130 the first sets of measurements. Different types of adjustments are possible, for instance:

- the computing device digitally modifies the predetermined unit arrangement, either by using the first sets of measurements or subsequent sets of measurements provided by the IMUs when the person performs a predetermined calibration movement;
- the computing device digitally rotates 180° the measurements provided by one or more units of the plurality of units for which the orientation is indicative of an upside-down arrangement;
- the computing device digitally modifies the biomechanical model based on at least the first sets of measurements so that, upon processing other measurements, the determination of whether any IMU is incorrectly arranged may be more precise;
- the computing device digitally modifies the biomechanical model for same purposes but based on a different set of measurements provided by the IMUs of the motion tracking system when the person performs a different predetermined movement, for example one for calibrating the biomechanical model;
- the person rearranges one or more units of the motion tracking system such that they are on the same body members of the person but in a different position in the body member and/or with different orientation; and/or
- the person rearranges two or more units of the motion tracking system such that they are on other body members of the person and, thus, the units may fulfill the predetermined unit arrangement.

The method 100 further comprises the subsequent step of the units each providing 150 a second set of measurements of the person (while the person has the units arranged 110 on the body members) performing a second predetermined movement that involves motion of one or more body members with a unit arranged thereon. The second predetermined movement comprises a movement or a sequence of movements for the physical rehabilitation of the person, thus the movement or movements are typically prescribed by a therapist that recommends which exercises may improve the physical condition of the tracked person.

The method 100 further comprises a subsequent step in which the computing device digitally processes 160 the second sets of measurements and determines whether the person has performed the second predetermined movement according to a set of predetermined movement constraints for the second predetermined movement.

The predetermined movement constraints are part of a physical exercise evaluation procedure such as, for example but without limitation, the evaluation procedure of patent document PCT/EP2019/066237, which is a procedure for determining a correct reproduction of a movement of a target based on a plurality of orientations thereof or one or more accelerations thereof at different time instants. Owing to predetermined constraints that define start and end angles, and/or start and end accelerations, it may be determined whether the person reproduces a given movement correctly (i.e. in accordance with the predetermined constraints). The movement is sometimes defined by more than one predetermined constraint that need be fulfilled by the tracked target in order to determine that the movement has been correctly reproduced.

In the event that the person did not properly arrange 110 the units on the different body members, the adjustment 140 of the operation of the motion tracking system causes a more accurate evaluation of the physical exercise of the person when performing the second predetermined movement so that the physical condition of the person may improve, therefore the risk of getting injured is reduced.

Figure 7:
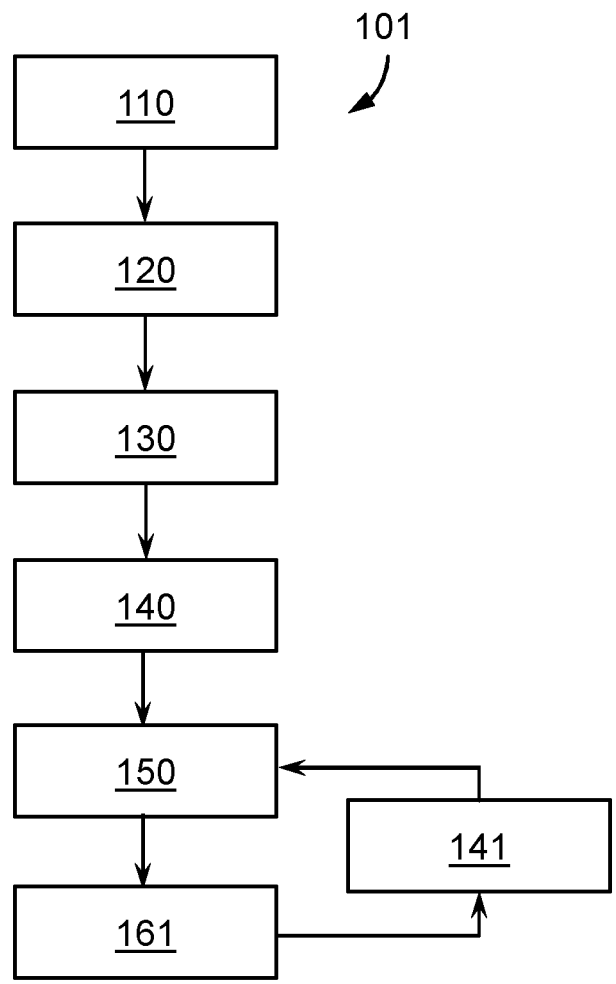

FIG. 7 diagrammatically shows a method 101 in accordance with an embodiment. The method 101 is similar to the method 100 of FIG. 6, but in this embodiment the motion tracking system evaluates the different sets of measurements provided by the IMUs in order to determine whether the units have been arranged improperly. Accordingly, the operation of the motion tracking system may be adjusted a plurality of times.

In particular, the second sets of measurements provided 150 by the units of the motion tracking system are digitally processed 161 by the computing device as follows. On the one hand, the computing device determines whether the person has performed the second predetermined movement according to the set of predetermined movement constraints for the second predetermined movement as described with reference to step 160 of FIG. 6. And, on the other hand, the computing device also determines if any unit has been incorrectly arranged on the person as done in step 130 of FIG. 6, but using at least the second sets of measurements; in some embodiments, the first sets of measurements or sets of measurements provided prior to the second sets of measurements may also be used in the determination of whether any unit has been incorrectly arranged.

This means that the motion tracking system is not only tracking and evaluating the physical exercise of the person, but also detecting whether the inertial measurement units have not been properly arranged on the body members (with respect to the predetermined unit arrangement and the predetermined position and orientation constraints) while the person is physically exercising.

In some embodiments, the computing device also determines, during the digital processing 161, that both: the person has not correctly performed the second predetermined movement due to measurements of particular one or more units not fulfilling the set of predetermined constraints for the second predetermined movement a predetermined number of times in a row, the particular one or more units being unit or units not supposed to move in the second predetermined movement; and the second sets of measurements of the particular one or more units is indicative of a reduced motion in each of these times.

The method 101 thus comprises a step of adjusting 141 the operation of the motion tracking system when the computing device has made any such determination while digitally processing 161 at least the second sets of measurements. The different types of adjustments described with reference to step 140 of FIG. 6 are also possible in this case. The adjustments 141 are preferably made before evaluating whether the person has correctly performed the predetermined movement so that if the computing device determines an incorrect arrangement of the IMUs that can be corrected by way of digital adjustments, the movement is evaluated with the correction already in place.

After having adjusted 141 the operation of the motion tracking system, any further predetermined movements to be performed by the person, for instance the second predetermined movement, will be evaluated more precisely. The sets of measurements provided by the IMUs when the person continues physically exercising are evaluated by the computing device in accordance with the predetermined movement constraints for the particular movement, but furthermore said sets of measurements can also be used by the computing device for additional adjustments of the motion tracking system. In some cases the IMUs change their position and/or orientation while the person is physically exercising, either because they have not been properly attached to the body members, or because the predetermined movements are so intense that they force the displacement of the IMUs, hence by detecting said changes and adjusting the operation of the motion tracking system a number of times the person is able to exercise with confidence.

In the event that the computing device determines that the units are properly arranged, no adjustments 141 are made to the operation of the motion tracking system and the person is able to continue physically exercising as well.

Concerning both the method 100 and the method 101 of FIGS. 6 and 7, in preferred embodiments, the computing device digitally produces feedback on how the person has physically exercised upon digitally processing 160, 161 the measurements corresponding to the performance of the second predetermined movement. The feedback may be provided to the person continuously (i.e. in real time or almost in real time while the person performs the predetermined movement) via presenting means, after having finished one or more predetermined movements, stored for ulterior analysis, and/or transmitted to another electronic device (for instance through an Internet connection) so that another person such as the therapist is able to review the activity of the tracked person.

Figure 8:
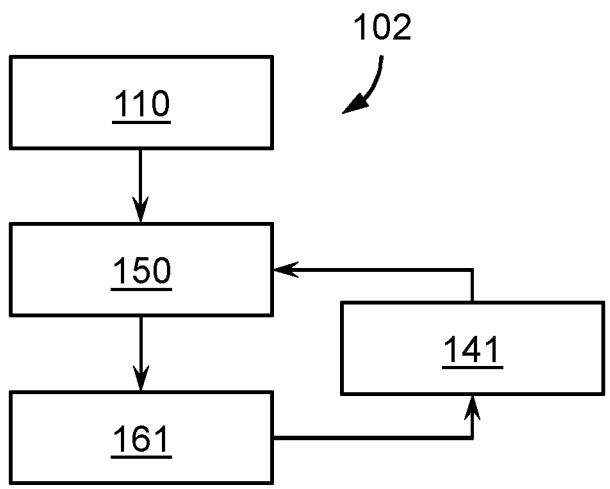

FIG. 8 diagrammatically shows a method 102 in accordance with an embodiment. The method 102 is similar to the method 101 of FIG. 7 but in this embodiment the first predetermined movement is the same as the second predetermined movement and is part of the physical exercises to be performed by the person for rehabilitation thereof.

Accordingly, once the IMUs have been arranged 110 on the body members of the person, the IMUs provide 150 sets of measurements of the person performing the second predetermined movement. The computing device digitally processes 161 these sets of measurements so as to determine whether the second predetermined movement has been correctly performed and also determines whether the IMUs have been properly arranged on the person. The operation of the motion tracking system is adjusted 141 if necessary (i.e. the computing device has determined that any unit is arranged on a body member of the person with an orientation outside of a predetermined orientation range for a unit on that body member, and/or that two or more units may be arranged on interchanged body members of the person according to the predetermined unit arrangement; and in some embodiments, also whether at least one body member of the person is in compliance with one or more predetermined criteria set for a biomechanical model digitally provided). The person then continues the physical exercise by performing the same movement or a different movement involving motion of at least one body member having a unit arranged thereon. Further sets of measurements are provided 150 for digital processing 161 by the computing device. Hence, the performance of predetermined movements, provision of measurements by the units, digital processing by the computing device and adjustments of the operation whenever necessary may be repeated a plurality of times, for instance until the person stops exercising.

In this text, the terms first, second, third, etc. have been used herein to describe several devices, elements or parameters, it will be understood that the devices, elements or parameters should not be limited by these terms since the terms are only used to distinguish one device, element or parameter from another. For example, the first predetermined movement could as well be named second predetermined movement, and the second predetermined movement could be named first predetermined movement without departing from the scope of this disclosure.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the disclosure as defined in the claims.

The invention claimed is:

1. A method for physical exercise of a person using a motion tracking system, the motion tracking system comprising a computing device and a plurality of units adapted to be arranged on body members of the person, each unit at least comprising an accelerometer and a gyroscope, the method comprising:

causing arrangement of each unit of the plurality of units on a different body member of the person;

providing, to the computing device, a first set of measurements of the person by each unit of the plurality of units, thereby enabling the computing device to obtain first sets of measurements, the first sets of measurements provided while the person is performing a first predetermined movement with the plurality of units arranged on the person, the first predetermined movement involving movement of at least one or more body members having a unit of the plurality of units arranged thereon; and digitally processing, by the computing device, at least the first sets of measurements so as to determine at least one of:

that a respective unit of the plurality of units is arranged on a body member of the person with an orientation outside of a predetermined orientation range for a unit on that body member, according to both a predetermined unit arrangement and at least one of predetermined acceleration or orientation constraints to be met by the respective unit when the person performs the first predetermined movement, at least based on one or more of accelerations or orientations measured by the respective unit; or that two or more units of the plurality of units are arranged on interchanged body members of the person, according to both the predetermined unit arrangement and at least one of predetermined acceleration or orientation constraints to be met by the two or more units when the person performs the first predetermined movement, at least based on one or more of the accelerations or the orientations measured by the two or more units;

in response to determining, based on at least the first sets of measurements that are provided while the person performs the first predetermined movement, at least one of that the respective unit of the plurality of units is arranged on the body member of the person with the orientation outside of the predetermined orientation range or that the two or more units are arranged on interchanged body members, adjusting operation of the motion tracking system, the operation being adjusted in such a way that at least one of:

the computing device digitally modifies, according to a determination made by the computing device at least based on one or more of the accelerations or the orientations measured by one or more of the plurality of units, at least one of: the predetermined unit arrangement or measurements provided by at least one of the plurality of units, the measurements digitally modified at least comprising measurements subsequent to the first sets of measurements; or at least one of the plurality of units is or are caused to be rearranged on the body members of the person, according to a determination made by the computing device at least based on one or more of the accelerations or the orientations measured by one or more of the plurality of units, to fulfill the predetermined unit arrangement;

providing a second set of measurements of the person by each unit of the plurality of units, thereby enabling the computing device to obtain second sets of measurements, the second sets of measurements provided while the person is performing a second predetermined movement with the plurality of units arranged on the person, the second predetermined movement involving movement of at least one or more body members having a unit of the plurality of units arranged thereon, the physical exercise comprising the second predetermined movement; and digitally processing, by the computing device, at least the second sets of measurements after the adjusting of the operation of the motion tracking system so as to determine whether the person has performed the second predetermined movement according to a set of predetermined movement constraints, the set of predetermined movement constraints comprising, at least for each of one or more body members that are to move in the second predetermined movement and to have a unit of the plurality of units arranged thereon according to the predetermined unit arrangement, one or more of: a predetermined movement orientation threshold or range, a predetermined movement motion threshold or range, or a predetermined movement acceleration threshold or range.

2. The method of claim 1, wherein:

the computing device digitally processes at least the second sets of measurements so as to further determine at least one of:

that a respective unit of the plurality of units is arranged on a body member of the person with an orientation outside of a predetermined orientation range for a unit on that body member, according to both the predetermined unit arrangement and one or more of predetermined acceleration or orientation constraints to be met by the respective unit when the person performs the second predetermined movement, at least based on one or more of accelerations or orientations measured by the respective unit; or that two or more units of the plurality of units are arranged on interchanged body members of the person, according to both the predetermined unit arrangement and one or more of predetermined acceleration or orientation constraints to be met by the two or more units when the person performs the second predetermined movement, at least based on one or more of the accelerations or the orientations measured by the two or more units;

the method further comprises, in response to determining, based on at least the second sets of measurements, at least one of that the respective unit of the plurality of units is arranged on the body member of the person with the orientation outside of the predetermined orientation range or that the two or more units are arranged on interchanged body members, adjusting the operation of the motion tracking system, the operation being adjusted in such a way that at least one of:

the computing device digitally modifies, according to a determination made by the computing device at least based on one or more of the accelerations or the orientations measured by one or more of the plurality of units, at least one of: the predetermined unit arrangement or measurements provided by at least one of the plurality of units, the measurements digitally modified at least comprising measurements subsequent to the second sets of measurements; or at least one of the plurality of units is or are caused to be rearranged on the body members of the person, according to a determination made by the computing device at least based on one or more of the accelerations or the orientations measured by one or more of the plurality of units, to fulfill the predetermined unit arrangement.

3. The method of claim 1, further comprising digitally providing, by the computing device, a biomechanical model representing body members and joints of a person; and wherein:

the computing device digitally processes the first sets of measurements so as to further determine whether at least one body member of the person complies with one or more predetermined criteria set for the biomechanical model, each criterion of the one or more predetermined criteria being indicative of one or more physical limitations of one or more body members; and the operation of the motion tracking system is further adjusted when the computing device determines, based on at least the first sets of measurements, that at least one body member complies with any one of one or more predetermined criteria set for the biomechanical model, the operation being adjusted in such a way that at least one of:

the computing device digitally modifies, according to a determination made by the computing device at least based on one or more of the accelerations or the orientations measured by one or more of the plurality of units and the one or more predetermined criteria complied with, the biomechanical model such that at least one of the body members and the joints represented therein have orientations of the measurements modified or measurements of units swapped so that they are assigned to other at least one of body members and joints of the biomechanical model; or one or more of the plurality of units is or are caused to be rearranged on the body members of the person, according to a determination made by the computing device at least based on one or more of the accelerations or the orientations measured by one or more of the plurality of units and the one or more predetermined criteria complied with, to fulfill the predetermined unit arrangement.

4. The method of claim 3, wherein the one or more predetermined criteria for the biomechanical model comprise that the at least one body member at least one of:

may have an orientation or may be moving following a motion that is not possible according to the biomechanical model;

may have an orientation during a first predetermined period of time that is uncomfortable according to the biomechanical model; or may have an orientation during a second predetermined period of time that according to the biomechanical model does not correspond to that of a person performing the first predetermined movement.

5. The method of claim 4, wherein at least one of:

the predetermined criterion whereby the at least one body member may have an orientation or may be moving following a motion that is not possible according to the biomechanical model comprises that an orientation of the body member at least exceeds a first predetermined orientation threshold, or that a linear or angular motion at least exceeds a first predetermined motion threshold;

the predetermined criterion whereby the at least one body member may have an orientation that is uncomfortable according to the biomechanical model comprises that an orientation of the body member at least exceeds a second predetermined threshold during the first predetermined period of time; or the predetermined criterion whereby the at least one body member may have an orientation that does not correspond to that of a person performing the first predetermined movement comprises that an orientation of the body member at least exceeds a third predetermined orientation threshold.

6. The method of claim 3, wherein an adjustment of the operation of the motion tracking system, when the computing device determines that the at least one body member complies with any one of the one or more predetermined criteria set for the biomechanical model, comprises at least one of:

digitally modifying, by the computing device, the biomechanical model based on the first sets of measurements such that at least one of the body members and the joints represented therein have orientations of the measurements modified by applying an angular correction factor, or measurements of units swapped so that they are assigned to other at least one of body members and joints of the biomechanical model;

providing a third set of measurements of the person by each unit of the plurality of units, thereby enabling the computing device to obtain third sets of measurements, the third sets of measurements provided while the person is performing a third predetermined movement with the plurality of units arranged on the person, the third predetermined movement involving movement of each body member having a unit of the plurality of units arranged thereon, and digitally modifying, by the computing device, the biomechanical model based on at least the third sets of measurements such that at least one of the body members and the joints represented therein have orientations of the measurements modified by applying an angular correction factor, or measurements of units swapped so that they are assigned to other at least one of body members and joints of the biomechanical model; or causing rearranging of two or more units of the plurality of units such that they are on other body members of the person to have the plurality of units arranged according to the predetermined unit arrangement.

7. The method of claim 6, wherein the computing device digitally modifies the biomechanical model based on the first sets of measurements when the computing device determines that the at least one body member may have an orientation or may be moving following a motion that is not possible according to the biomechanical model.

8. The method of claim 1, wherein the adjustment of the operation of the motion tracking system further comprises at least one of:

digitally modifying, by the computing device, the predetermined unit arrangement by changing a correspondence between units and body members in the predetermined unit arrangement;

digitally rotating 180°, by the computing device, the measurements provided by one or more units of the plurality of units arranged upside-down with respect to the predetermined unit arrangement;

rearranging the respective unit having the orientation outside of the predetermined orientation range such that the respective unit is arranged on a same body member but at least one of in a different position thereof or with a different orientation to fulfill the predetermined unit arrangement; or rearranging the two or more units of the plurality of units such that they are on other body members of the person to fulfill the predetermined unit arrangement.

9. The method of claim 1, wherein the physical exercise further comprises the first predetermined movement, and the computing device digitally processes the first sets of measurements so as to further determine whether the person has performed the first predetermined movement according to a set of predetermined movement constraints for the first predetermined movement.

10. A motion tracking system comprising:

a computing device comprising at least one processor and at least one memory; and a plurality of units adapted to be arranged on body members of a person, each unit at least comprising an accelerometer and a gyroscope;

wherein the at least one processor is configured, together with the at least one memory, to perform operations comprising:

processing first sets of measurements of the person comprising at least a first set of measurements provided by each unit of the plurality of units, the first sets of measurements provided while the person is performing a first predetermined movement with the plurality of units arranged on the person, the first predetermined movement involving movement of at least one or more body members having a unit of the plurality of units arranged thereon, and the processing being so as to determine at least one of:

that a respective unit of the plurality of units is arranged on a body member of the person with an orientation outside of a predetermined orientation range for a unit on that body member, according to both a predetermined unit arrangement and at least one of predetermined acceleration or orientation constraints to be met by the respective unit when the person performs the first predetermined movement, at least based on one or more of accelerations or orientations measured by the respective unit; or that two or more units of the plurality of units are arranged on interchanged body members of the person, according to both the predetermined unit arrangement and at least one of predetermined acceleration or orientation constraints to be met by the two or more units when the person performs the first predetermined movement, at least based on one or more of the accelerations or the orientations measured by the two or more units;

in response to determining, based on at least the first sets of measurements that are provided while the person performs the first predetermined movement, at least one of that the respective unit of the plurality of units is arranged on the body member of the person with the orientation outside of the predetermined orientation range or that the two or more units are arranged on interchanged body members, adjusting operation of the motion tracking system, the operation being adjusted in such a way that at least one of:

the at least one processor digitally modifies, according to the determination made at least based on one or more of the accelerations or the orientations measured by one or more of the plurality of units, at least one of: the predetermined unit arrangement or measurements provided by at least one of the plurality of units, the measurements digitally modified at least comprising measurements subsequent to the first sets of measurements; or the at least one processor causes to provide at least one user perceptible signal indicating that at least one of the plurality of units is or are arranged on interchanged body members of the person or indicating how to rearrange the at least one of the plurality of units on the body members of the person to fulfill the predetermined unit arrangement according to the determination made at least based on one or more of the accelerations or the orientations measured by one or more of the plurality of units; and processing at least second sets of measurements after the adjustment of the operation of the motion tracking system, each second set of measurements in the second sets of measurements being provided by a unit of the plurality of units while the person is performing a second predetermined movement with the plurality of units arranged on the person, the second predetermined movement involving movement of at least one or more body members having a unit of the plurality of units arranged thereon, a physical exercise performed by the person comprising the second predetermined movement, and the processing being so as to determine whether the person has performed the second predetermined movement according to a set of predetermined movement constraints, the set of predetermined movement constraints comprising, at least for each of one or more body members that are to move in the second predetermined movement and to have a unit of the plurality of units arranged thereon according to the predetermined unit arrangement, one or more of: a predetermined movement orientation threshold or range, a predetermined movement motion threshold or range, or a predetermined movement acceleration threshold or range.

11. The motion tracking system of claim 10, the operations further comprising:

processing at least the second sets of measurements so as to further determine at least one of:

that a respective unit of the plurality of units is arranged on a body member of the person with an orientation outside of a predetermined orientation range for a unit on that body member, according to both the predetermined unit arrangement and one or more of predetermined acceleration or orientation constraints to be met by the respective unit when the person performs the second predetermined movement, at least based on one or more of accelerations or orientations measured by the respective unit; or that two or more units of the plurality of units are arranged on interchanged body members of the person, according to both the predetermined unit arrangement and one or more of predetermined acceleration or orientation constraints to be met by the two or more units when the person performs the second predetermined movement, at least based on one or more of the accelerations or the orientations measured by the two or more units; and in response to determining, based on at least the second sets of measurements, at least one of that the respective unit of the plurality of units is arranged on the body member of the person with the orientation outside of the predetermined orientation range or that the two or more units are arranged on interchanged body members, adjusting the operation of the motion tracking system, the operation being adjusted in such a way that at least one of:

the at least one processor digitally modifies, according to the determination made at least based on one or more of the accelerations or the orientations measured by one or more of the plurality of units, at least one of: the predetermined unit arrangement or measurements provided by at least one of the plurality of units, the measurements digitally modified at least comprising measurements subsequent to the second sets of measurements; or the at least one processor causes to provide at least one user perceptible signal indicating that at least one of the plurality of units is or are arranged on interchanged body members of the person or indicating how to rearrange the at least one of the plurality of units on the body members of the person to fulfill the predetermined unit arrangement according to the determination made at least based on one or more of the accelerations or the orientations measured by one or more of the plurality of units.

12. The motion tracking system of claim 10, the operations further comprising:

digitally providing a biomechanical model representing body members and joints of a person; and wherein:

the at least one processor digitally processes the first sets of measurements so as to further determine whether at least one body member of the person complies with one or more predetermined criteria set for the biomechanical model, each criterion of the one or more predetermined criteria being indicative of one or more physical limitations of one or more body members; and the operation of the motion tracking system is further adjusted when the at least one processor determines, based on at least the first sets of measurements, that at least one body member complies with any one of the one or more predetermined criteria set for the biomechanical model, the operation being adjusted by at least one of:
  digitally modifying, according to the determination made by the at least one processor at least based on one or more of the accelerations or the orientations measured by one or more of the plurality of units and the one or more predetermined criteria complied with, the biomechanical model such that at least one of the body members and the joints represented therein have orientations of the measurements modified or measurements of units swapped so that they are assigned to other at least one of body members and joints of the biomechanical model; and
  the at least one processor causes to provide at least one user perceptible signal indicating that at least one of the plurality of units is or are arranged on interchanged body members of the person or indicating how to rearrange the at least one of the plurality of units on the body members of the person to fulfill the predetermined unit arrangement according to a determination made at least based on one or more of the accelerations or the orientations measured by one or more of the plurality of units and the one or more predetermined criteria complied with.

13. The motion tracking system of claim 12, wherein the one or more predetermined criteria for the biomechanical model comprise that the at least one body member at least one of:
  may have an orientation or may be moving following a motion that is not possible according to the biomechanical model;
  may have an orientation during a first predetermined period of time that is uncomfortable according to the biomechanical model; or
  may have an orientation during a second predetermined period of time that according to the biomechanical model does not correspond to that of a person or performing the first predetermined movement.

14. The motion tracking system of claim 13, wherein at least one of:
  the predetermined criterion whereby the at least one body member may have an orientation or may be moving following a motion that is not possible according to the biomechanical model comprises that an orientation of the body member at least exceeds a first predetermined orientation threshold, or that a linear or angular motion at least exceeds a first predetermined motion threshold;
  the predetermined criterion whereby the at least one body member may have an orientation that is uncomfortable according to the biomechanical model comprises that an orientation of the body member at least exceeds a second predetermined threshold during the first predetermined period of time; or
  the predetermined criterion whereby the at least one body member may have an orientation that does not correspond to that of a person performing the first predetermined movement comprises that an orientation of the body member at least exceeds a third predetermined orientation threshold.

15. The motion tracking system of claim 12, wherein an adjustment of the operation of the motion tracking system, when the at least one processor determines that the at least one body member complies with any one of the one or more predetermined criteria set for the biomechanical model, comprises at least one of:
  digitally modifying the biomechanical model based on the first sets of measurements such that at least one of the body members and the joints represented therein have orientations of the measurements modified by applying an angular correction factor, or measurements of units swapped so that they are assigned to other at least one of body members and joints of the biomechanical model;
  digitally modifying the biomechanical model based on at least third sets of measurements such that at least one of the body members and the joints represented therein have orientations of the measurements modified by applying an angular correction factor, or measurements of units swapped so that they are assigned to other at least one of body members and joints of the biomechanical model, wherein each third set of measurements in the third sets of measurements is provided by a unit of the plurality of units while the person is performing a third predetermined movement with the plurality of units arranged on the person, the third predetermined movement involving movement of each body member having a unit of the plurality of units arranged thereon; or
  causing to provide, by the at least one processor, at least one user perceptible signal indicating that two or more of the plurality of units are to be rearranged on other body members to have the plurality of units arranged according to the predetermined unit arrangement.

16. The motion tracking system of claim 15, wherein the at least one processor digitally modifies the biomechanical model based on the first sets of measurements when the at least one processor determines that the at least one body member may have an orientation or may be moving following a motion that is not possible according to the biomechanical model.

17. The motion tracking system of claim 10, wherein the physical exercise further comprises the first predetermined movement, and the at least one processor digitally processes the first sets of measurements so as to further determine whether the person has performed the first predetermined movement according to a set of predetermined movement constraints for the first predetermined movement.

18. A non-transitory computer-readable storage medium comprising instructions which, when executed by a device, cause the device to perform operations comprising:
  processing first sets of measurements of a person comprising at least a first set of measurements provided by each unit of a plurality of units of a motion tracking system with each unit at least comprising an accelerometer and a gyroscope, the first sets of measurements being provided while the person is performing a first predetermined movement with the plurality of units arranged on body members of the person, the first predetermined movement involving movement of at least one or more body members having a unit of the plurality of units arranged thereon, and the processing being so as to determine at least one of:
    that a respective unit of the plurality of units is arranged on a body member of the person with an orientation outside of a predetermined orientation range for a unit on that body member, according to both a predetermined unit arrangement and at least one of predetermined acceleration or orientation constraints to be met by the respective unit when the person performs the first predetermined movement, at least based on one or more of accelerations or orientations measured by the respective unit; or that two or more units of the plurality of units are arranged on interchanged body members of the person, according to both the predetermined unit arrangement and at least one of predetermined acceleration or orientation constraints to be met by the two or more units when the person performs the first predetermined movement, at least based on one or more of the accelerations or the orientations measured by the two or more units;

in response to determining, based on at least the first sets of measurements, at least one of that the respective unit of the plurality of units is arranged on the body member of the person with the orientation outside of the predetermined orientation range or that the two or more units are arranged on interchanged body members, adjusting operation of the motion tracking system upon determining, the operation being adjusted by at least one of:

digitally modifying, according to the determination made at least based on one or more of the accelerations or the orientations measured by one or more of the plurality of units, at least one of: the predetermined unit arrangement or measurements provided by at least one of the plurality of units, the measurements digitally modified at least comprising measurements subsequent to the first sets of measurements; and causing to provide at least one user perceptible signal indicating that at least one of the plurality of units is or are arranged on the interchanged body members of the person or indicating how to rearrange the at least one of the plurality of units on the body members of the person to fulfill the predetermined unit arrangement according to a determination made by the device at least based on one or more of the accelerations or the orientations measured by one or more of the plurality of units; and processing at least second sets of measurements after the adjustment of the operation of the motion tracking system, each second set of measurements in the second sets of measurements being provided by a unit of the plurality of units while the person is performing a second predetermined movement with the plurality of units arranged on the person, the second predetermined movement involving movement of at least one or more body members having a unit of the plurality of units arranged thereon, a physical exercise performed by the person comprising the second predetermined movement, and the processing being to determine whether the person has performed the second predetermined movement according to a set of predetermined movement constraints, the set of predetermined movement constraints comprising, at least for each of one or more body members that are to move in the second predetermined movement and to have a unit of the plurality of units arranged thereon according to the predetermined unit arrangement, one or more of: a predetermined movement orientation threshold or range, a predetermined movement motion threshold or range, or a predetermined movement acceleration threshold or range.

19. The non-transitory computer-readable storage medium of claim 18, the operations further comprising:

processing at least the second sets of measurements so as to further determine at least one of:

that a respective unit of the plurality of units is arranged on a body member of the person with an orientation outside of a predetermined orientation range for a unit on that body member, according to both the predetermined unit arrangement and one or more of predetermined acceleration or orientation constraints to be met by the respective unit when the person performs the second predetermined movement, at least based on one or more of accelerations or orientations measured by the respective unit; or that two or more units of the plurality of units are arranged on interchanged body members of the person, according to both the predetermined unit arrangement and one or more of predetermined acceleration or orientation constraints to be met by the two or more units when the person performs the second predetermined movement, at least based on one or more of the accelerations or the orientations measured by the two or more units;

in response to determining, based on at least the second sets of measurements, at least one of that the respective unit of the plurality of units is arranged on the body member of the person with the orientation outside of the predetermined orientation range or that the two or more units are arranged on interchanged body members, adjusting the operation of the motion tracking system, the operation being adjusted by at least one of:

digitally modifying, according to the determination made at least based on one or more of the accelerations or the orientations measured by one or more of the plurality of units, at least one of: the predetermined unit arrangement or measurements provided by at least one of the plurality of units, the measurements digitally modified at least comprising measurements subsequent to the second sets of measurements; or causing to provide at least one user perceptible signal indicating that at least one of the plurality of units is or are arranged on interchanged body members of the person or indicating how to rearrange the at least one of the plurality of units on the body members of the person to fulfill the predetermined unit arrangement according to the determination made at least based on one or more of the accelerations or the orientations measured by one or more of the plurality of units.

20. The non-transitory computer-readable storage medium of claim 18, the operations further comprising:

providing a biomechanical model representing body members and joints of a person; and wherein:

the device processes the first sets of measurements so as to further determine whether at least one body member of the person complies with one or more predetermined criteria set for the biomechanical model, each criterion of the one or more predetermined criteria being indicative of one or more physical limitations of one or more body members; and the operation of the motion tracking system is further adjusted upon determining, based on at least the first sets of measurements, that at least one body member complies with any one of one or more predetermined criteria set for the biomechanical model, the operation being adjusted by at least one of:

digitally modifying, according to the determination made at least based on one or more of the accelerations or the orientations measured by one or more of the plurality of units and the one or more predetermined criteria complied with, the biomechanical model such that at least one of the body members and the joints represented therein have orientations of the measurements modified or measurements of units swapped so that they are assigned to other at least one of body members and joints of the biomechanical model; or causing to provide at least one user perceptible signal indicating that at least one the plurality of units is or are arranged on interchanged body members of the person or indicating how to rearrange the at least one of the plurality of units on the body members of the person to fulfill the predetermined unit arrangement according to a determination made at least based on one or more of the accelerations or the orientations measured by one or more of the plurality of units and the one or more predetermined criteria complied with.

* * * * *